US007648471B2

(12) United States Patent
Hobson

(10) Patent No.: US 7,648,471 B2
(45) Date of Patent: Jan. 19, 2010

(54) MEDICAL APPARATUS, USE AND METHODS

(75) Inventor: Barry Reginald Hobson, Western Australia (AU)

(73) Assignee: Merlex Corporation Pty Ltd., Bentley (AU)

( * ) Notice: Subject to any disclaimer, the term of this patent is extended or adjusted under 35 U.S.C. 154(b) by 445 days.

(21) Appl. No.: 11/285,890

(22) Filed: Nov. 22, 2005

(65) Prior Publication Data

US 2006/0106313 A1    May 18, 2006

Related U.S. Application Data

(63) Continuation of application No. PCT/AU2004/000680, filed on May 21, 2004.

(30) Foreign Application Priority Data

May 22, 2003   (AU) .............................. 2003902503

(51) Int. Cl.
*A61H 1/00* (2006.01)
*A61H 7/00* (2006.01)
*A61H 19/00* (2006.01)
(52) U.S. Cl. ............................ 601/78; 601/84; 601/151
(58) Field of Classification Search .................. 601/46, 601/48, 66, 69, 70, 78, 81, 84–90, 100, 101, 601/148–151, 166; 606/201–203
See application file for complete search history.

(56) References Cited

U.S. PATENT DOCUMENTS 2,949,108 A * 8/1960 Vecchio ........................ 601/18
3,547,102 A * 12/1970 Frenkel et al. .............. 600/575
3,599,631 A * 8/1971 Werding ....................... 601/18
4,003,371 A * 1/1977 Fischer ......................... 604/23

(Continued)

FOREIGN PATENT DOCUMENTS

DE    20445605    3/2002

(Continued)

OTHER PUBLICATIONS

International Search Report for PCT Application No. PCT/AU2004/000680.

(Continued)

*Primary Examiner*—Justine R Yu
*Assistant Examiner*—Kristen C Matter
(74) *Attorney, Agent, or Firm*—Klarquist Sparkman, LLP

(57) ABSTRACT

In accordance with one embodiment, a vibratory transducer has an armature suspended in a magnetic field. The armature has a plurality of electrical conductive paths to provide electrical current flow in said armature to react with said magnetic field and cause movement in the armature controlled by variation in the electrical current flow. A contact surface is secured to the armature, with a surface area for frictionally coupling to a corresponding surface area of a patient for example. Movement of the vibratory transducer induces movement in the patient, and the transducer can produce movement in the contact surface in at least two dimensions simultaneously. In one embodiment the contact surface is flat, while in alternative embodiments the contact surface is incorporated in a toroidal structure so as to surround part of the patient. Medical application can include treatment of bone fractures, oedema, and in elastography, amongst other applications.

18 Claims, 19 Drawing Sheets

U.S. PATENT DOCUMENTS

| | | | | |
|---|---|---|---|---|
| 4,005,703 | A | * | 2/1977 | Rosen et al. .................. 601/57 |
| 4,711,229 | A | | 12/1987 | Hengl |
| 5,468,218 | A | | 11/1995 | Ward |
| 5,474,070 | A | | 12/1995 | Ophir et al. |
| 6,001,055 | A | | 12/1999 | Souder |
| 6,007,559 | A | * | 12/1999 | Arkans ....................... 606/201 |
| 6,486,669 | B1 | | 11/2002 | Sinkus et al. |
| 6,488,626 | B1 | | 12/2002 | Lizzi et al. |
| 7,252,644 | B2 | * | 8/2007 | Dewald et al. ................ 601/5 |
| 7,377,896 | B2 | * | 5/2008 | Dykers, Jr. .................. 600/38 |
| 2003/0109771 | A1 | * | 6/2003 | Forsell ....................... 600/38 |

FOREIGN PATENT DOCUMENTS

| | | |
|---|---|---|
| EP | 0513508 | 11/1992 |
| JP | 2000135263 | 5/2000 |
| JP | 2002159556 | 6/2002 |
| WO | WO02065973 | 8/2002 |

OTHER PUBLICATIONS

International Preliminary Report on Patentability for PCT Application No. PCT/AU2004/000680.

* cited by examiner

MEDICAL APPARATUS, USE AND METHODS

CROSS-REFERENCE TO RELATED APPLICATIONS

The present application is a continuation of International Application No. PCT/AU2004/000680, filed May 21, 2004, which claims the benefit of Australian Application No. 2003902503, filed May 22, 2003.

FIELD

This invention relates to the field of medical apparatus, and particularly apparatus for imaging, and treatment. In particular this invention relates to use of a transducer for such imaging and treatment.

This invention has particular application in imaging techniques such as sonoelastography, and treatment of conditions such as osteoporosis and oedemas such as lymphoedema.

BACKGROUND ART

Sonoelastography is an ultrasound imaging technique where low amplitude, and low frequency shear waves are propagated through organs and tissue while real time Doppler techniques are used to image the resulting vibration pattern. Hard lesions such as tumours in the presence of soft tissue, such in breast cancer, will have reduced vibration amplitude, which is readily imaged by ultrasonic means.

Malignant tumours manifest themselves by way of pathological changes such as variation in the tissue's mechanical stiffness, which can be detected by a reduction in strain as compared to the surrounding soft tissue.

An existing technique known as "elastography" is used in breast tumour diagnosis whereby ultrasonic echo data is collected before and after a slight "compression" of the tissue. Comparisons can be made between normal and pathologically affected tissue by gathers information on the static elastic properties of the tissue before and during compression. The differing elastic properties between a benign and malignant tumour can be distinguished by an ultrasound echo detection device.

In yet another area of research, it has been documented that a rapidly changing strain or vibration applied to the tissue will result in more defined differences between healthy and pathological tissue. To better distinguish variations in tissue elastic properties, the vibrational frequency response is dependant upon the induced excitation frequency and the amplitude of the vibration source.

Variations in tissue motion can be detected by frequency shifts in ultrasonic echoes and imaged using conventional 2D ultrasound scanners and Doppler ultrasound scanners; a method commonly used to highlight blood flow.

The apparatus of the present disclosure also has application in treatment of osteoporosis. The skeletal bone structure of a human is considered to be a frameworks of levers upon which muscles are attach to enable movement of the whole body. The skeletal bones are subjected to many varying vibrations due to locomotion, bodily functions, stress, strain and also due to the anchorage of muscle fibres and tendons which are continuously vibrating at different frequencies depending upon the strain applied to them. Bones are subjected to compression influences and vibration during the act of walking, running and jumping and these vibrations reverberate up through the skeletal structure passing through the whole body.

It is well documented that bone metabolism is responsive and triggered by mechanical strain. Mechanical loads can be applied through weight bearing exercise or they can be applied by mechanical external sources to the body to cause in vivo deformations of the bone. It is this deformation that signals the bone cells to remodel (rebuild or adapt) the skeletal structure to accommodate the strain applied. This biological phenomenon has long been recognised by physicians for the prevention and treatment of the bone loss condition known as osteoporosis.

In the 1890's Julius Wolff a German anatomist, claimed that bone structure could adapt in response to a changing mechanical environment and that the orientation of trabeculae could be changed if there was a change in mechanical stress directions. The biological response of bone to mechanical loading is a complex function and differs according to the individual, the magnitude and the pattern and "direction of the stress" applied. Dynamic mechanical loading leads to interstitial fluid flow within the fluid spaces of bone which plays an important role in providing hydrostatic shear pressure to activate the bone cells into remodelling action.

Traditional vibration devices are in the form of one-dimensional acoustic speaker type transducers whereby the vibration is delivered in the form of a linear stroke in the "z" or vertical axis. This form of vibration transducer can vary the frequency output but cannot offer any variation to the mono dimensional amplitude. When used in sonoelastography, the vibration source of this type is required to be repositioned many times during scanning to improve the quality of the 3D mapping reconstruction and to reduce the shadowing effect. Another disadvantage of this form of vibration is that it can generate modal patterns which can make image interpretation difficult.

In treatment of osteoporosis, prior art stimulating devices consist of transducer type, vertically moving platforms, which the patient either stands or sits upon. This method applies a compression load to the bones which is converted to a measure of micro-strains by determining the change in the bones length divided by the original bone length. This compression load must be of a significant force to reflect a change in the length of a bones due to the bone matrix being far stronger in compression than in shear. These prior art transducer methods of applying a vertical compressive stress to the skeletal structure have limited success in applying mechanical stimulus to the wider range of bones such as ribs and short plate like pelvic and hip bones to affect a change in bone rebuilding. With this form of shock loading the joints and cartilages must also endure the stress and further transmit the vibration along to the next set of bones for them to benefit from the stress stimulus.

Throughout the specification, unless the context requires otherwise, the word "comprise" or variations such as "comprises" or "comprising", will be understood to imply the inclusion of a stated integer or group of integers but not the exclusion of any other integer or group of integers.

SUMMARY

In accordance with one embodiment there is provided, in medical application, use of a vibratory transducer having at least two dimensions of movement available simultaneously, said vibratory transducer having contact surface with a surface area for frictionally coupling to a corresponding surface area of a patient, where movement of said vibratory transducer induces movement in the patient.

Also in accordance with a second embodiment there is provided a vibratory transducer for medical application, said vibratory transducer having an armature suspended in a magnetic field, said armature having a plurality of electrical conductive paths to provide electrical current flow in said armature to react with said magnetic field, said vibratory transducer having a contact surface secured to said armature, said contact surface having a surface area for frictionally coupling to a corresponding surface area of a patient, where movement of said vibratory transducer induces movement in the patient, and wherein said transducer can produce movement in said contact surface in at least two dimensions simultaneously.

Preferably said at least two dimensions of movement comprises two translational dimensions of movement in a single plane.

In one preferred arrangement of either embodiment, the contact surface is toroidal, and encases the patient or part of the patient. Preferably in this form, the contact surface has an internal configuration adapted to closely conform with the anatomy of the patient, and so maximise the contact area with the patient.

In an alternative preferred arrangement of either embodiment, the contact surface is preferably flat. In such an arrangement, the patient will stand, sit, or lie on the contact surface, allowing vibrations to pass from the contact surface to the patient. The effect of having a surface area in contact with the patient is to increase the extent and accuracy of the movement induced in the patient, in two, and especially in three dimensions.

Thus, also in accordance with a third embodiment there is provided, in medical application, use of a vibratory transducer having an armature relative to a magnetic flux and producing at least two dimensions of movement in the same plane as said armature, said vibratory transducer having connected with said armature, a contact surface with a surface area for frictionally coupling to a corresponding surface area of a patient, where movement of said vibratory transducer induces movement in the patient.

Also, in accordance with a fourth embodiment there is provided, in medical application, use of a vibratory transducer having a platform capable of at least two dimensions of movement relative to a magnetic flux in a single plane containing said platform, said magnetic flux being formed by oppositely disposed magnetic poles, said vibratory transducer having a contact surface with a surface area for frictionally coupling to a corresponding surface area of a patient, where movement of said vibratory transducer induces movement in the patient.

Also in accordance with a fifth embodiment there is provided a vibratory transducer for medical application, said vibratory transducer having an armature suspended in a magnetic flux, said armature having a plurality of electrical conductive paths to provide electrical current flow in said armature to react with said magnetic flux, said transducer having a contact surface secured to said armature, said contact surface having a surface area for frictionally coupling to a corresponding surface area of a patient, where movement of said vibratory transducer induces movement in the patient, wherein said transducer produces movement in said contact surface in at least two dimensions.

Preferably said at least two dimensions of movement consists of translational movement along x and y axes in a common plane.

Preferably said at least two dimensions of movement includes movement in a third dimension along a z axis normal to said x and y axes.

Preferably said medical application is selected from medical imaging such as sonoelastography, and medical treatment such as treatment of oedemas, lymphoedema, muscle and tissue conditions, treatment of bone breakage, fractures, and osteoporosis.

In a further embodiment there is provided a method of treating a patient having affected tissue, the method comprising subjecting the patient to a complex pressure stimulus operating in multiple directions, the stimulus stimulating the epidermis, dermis and subcutaneous layers of the affected tissue such that there is a relatively rapid movement of interstitial fluid in the affected tissue into the lymphatic system.

In preferred arrangements the pressure stimulus is not spherical, cycloidal or linear, and follows a path containing at least three non-colinear points for each cycle of stimulation.

In another embodiment the pressure stimulus includes pressure variations directed substantially along a path that is arranged within an area and which substantially avoids travelling back and forth over a central region of the area.

The path may consist of twenty path elements arranged end to end, with each end positioned to lie substantially on a circle such that the twenty path elements form a continuous and substantially symmetrical twenty-pointed star. With this arrangement the method may achieve a movement of 80 milliliters of interstitial fluid into the lymphatic system in less than a 30 minute treatment session. In one particularly preferred arrangement about 80 milliliters of interstitial fluid is moved into the lymphatic system in less than a 10 minute treatment session.

Preferably the pressure stimulus includes pressure variations directed substantially along a continuous path and the total absolute angular displacement over the path is more than 360 degrees. In one arrangement the total absolute angular displacement over the path is about 540 degrees. In another arrangement the total absolute angular displacement over the path is about 720 degrees.

Preferably there are at least two distinct changes in direction over a cycle of oscillation of the pressure stimulus.

The epidermis, dermis and subcutaneous layers of the affected tissue may be stimulated to the extent that a ripple effect is induced along the surface of the patient's skin away from the stimulus. Without being limited to a particular theory it is thought that the method operates to stimulate the anchoring filaments of the initial lymphatics in a concerted manner so as to influence the opening of the endothelial cell gates of the initial lymphatics and thereby cause the relatively rapid movement of interstitial fluid.

With the advantages of the system, preferred arrangements may limit the pressure stimulus to ensure that the movement of interstitial fluid into the lymphatic system is controlled and is not so rapid as to adversely affect the patient. To assist with rapidly and controllably moving interstitial fluid into the lymphatic system the method may include receiving response information from the epidermis and adjusting the pressure stimulus according to the response information and predetermined criteria.

The stimulus may be applied to a relatively thin band around a limb of the patient and the ripple effect may extend at least to where the limb is connected to the body of the patient.

In some arrangements the method includes selecting a resonant frequency of the layers of tissue and subjecting the patient to a stimulus at that frequency. To improve the patient response the anchoring filaments of the initial lymphatics may be stimulated in a concerted manner over a range of sweeping frequencies so as to influence the opening of the endothelial cell gates of the initial lymphatics and thereby cause the relatively rapid movement of interstitial fluid in the affected tissue into the lymphatic system.

In one arrangement the layers of tissue are stimulated at magnitude of between about 0.1 mm and about 5 mm, peak to peak, and at a frequency of between about 10 and 100 Hz. The pressure stimulus may be applied from a base point moving at a velocity of about 100 mm per second. In another arrangement the layers of tissue are stimulated a magnitude of between about 0.5 mm and about 5 mm, peak to peak, and at a frequency of between about 1 and 50 Hz.

The pressure variations may be two dimensional by virtue of the area comprising a surface arranged substantially perpendicular to the length of a body part or limb of the patient which is being treated. Furthermore, the path may consists of five path elements arranged end to end, with each end positioned to lie substantially on a circle, such that the five path elements form a continuous and substantially symmetrical five pointed star. Each path element may comprise a line that is slightly curved so as to have rounded points.

Alternatively the path may consists of three lines arranged end to end, with each end positioned to lie substantially on a circle, such that three path elements form a continuous and substantially symmetrical triangle.

In one particularly preferred arrangement the path consists of twenty path elements arranged end to end, with each end positioned to lie substantially on a circle such that the twenty path elements form a continuous and substantially symmetrical twenty-pointed star. As would be apparent in this arrangement there many more than at least two distinct changes in direction over a cycle of oscillation of the pressure stimulus.

The method may including translating a member that surrounds the limb of the patient, the member being translated to create the pressure variations. Preferably the member is substantially rigid.

According to another embodiment there is provided a method of treating a patient having affected tissue, the method comprising subjecting the patient to a complex pressure stimulus operating in multiple directions, the stimulus stimulating the epidermis, dermis and subcutaneous layers of the affected tissue such that the anchoring filaments of the initial lymphatics vibrate in a relatively rapid manner that is conducive to stimulating a resetting of their elastic properties.

Preferably the pressure stimulus is not spherical, cycloidal or linear, and follows a path of at least three non-colinear points for each cycle of stimulation.

A ripple effect along the surface of the skin away from the stimulus may evident. Thus, according to yet another embodiment there is provided a method of treating a patient having affected tissue, the method comprising: subjecting the patient to a pressure stimulus operating in multiple directions such that a ripple effect along the surface of the skin away from the stimulus is evident, which method includes, and the ripple effect being indicative of, the epidermis, dermis and subcutaneous layers of the affected tissue being stimulated by the stimulus in multiple directions so that the anchoring filaments of the initial lymphatics vibrate in a relatively rapid manner that is conducive to stimulating a resetting of their elastic properties.

According to a yet another embodiment there is provided apparatus for treating a patient having affected tissue, the apparatus including a plurality of compartments that are adapted to surround and closely conform to a limb of the patient, the compartments being substantially isolated from each other so that each compartment is able to apply a relatively independent pressure stimulus at particular locations around the limb.

Preferably particular compartments can be rendered inoperable so as to avoid stimulating a sensitive area of the limb, and the compartments may be adapted to dynamically adjust to the limb during treatment so as to maintain an pressure stimulus that is appropriate for the size and condition of the limb.

The apparatus may include a receiver for receiving response information from the patient and control means for adjusting the pressure stimulus according to the response information and predetermined criteria. The predetermined criteria may be formulated for ensuring that the movement of interstitial fluid into the lymphatic system is controlled so as to gain a relatively maximum patient response and meter the rate of transfer not to be adverse to the patient.

According to yet another embodiment there is provided a method of preventing secondary lymphoedema including subjecting the patient to a complex pressure stimulus operating in multiple directions such that the epidermis, dermis and subcutaneous layers of the affected tissue are stimulated to the extent that there is a flexure in the tissue at a magnitude between about 0.5 mm and 3 mm, peak to peak, at a frequency of between about 1 and 50 Hz. Preferably, if the method were to be applied to a case of primary lymphoedema there would be a relatively rapid movement of interstitial fluid in the affected tissue into the lymphatic system.

Insight into the advantages and characteristics of the present invention can be gained from the following description of preferred embodiments and the accompanying drawings. Further aspects and preferred features may be apparent.

BRIEF DESCRIPTION OF THE DRAWINGS

Several embodiments of the invention will now be described in the following description made with reference to the drawings, in which.

DETAILED DESCRIPTION

Figure 1:
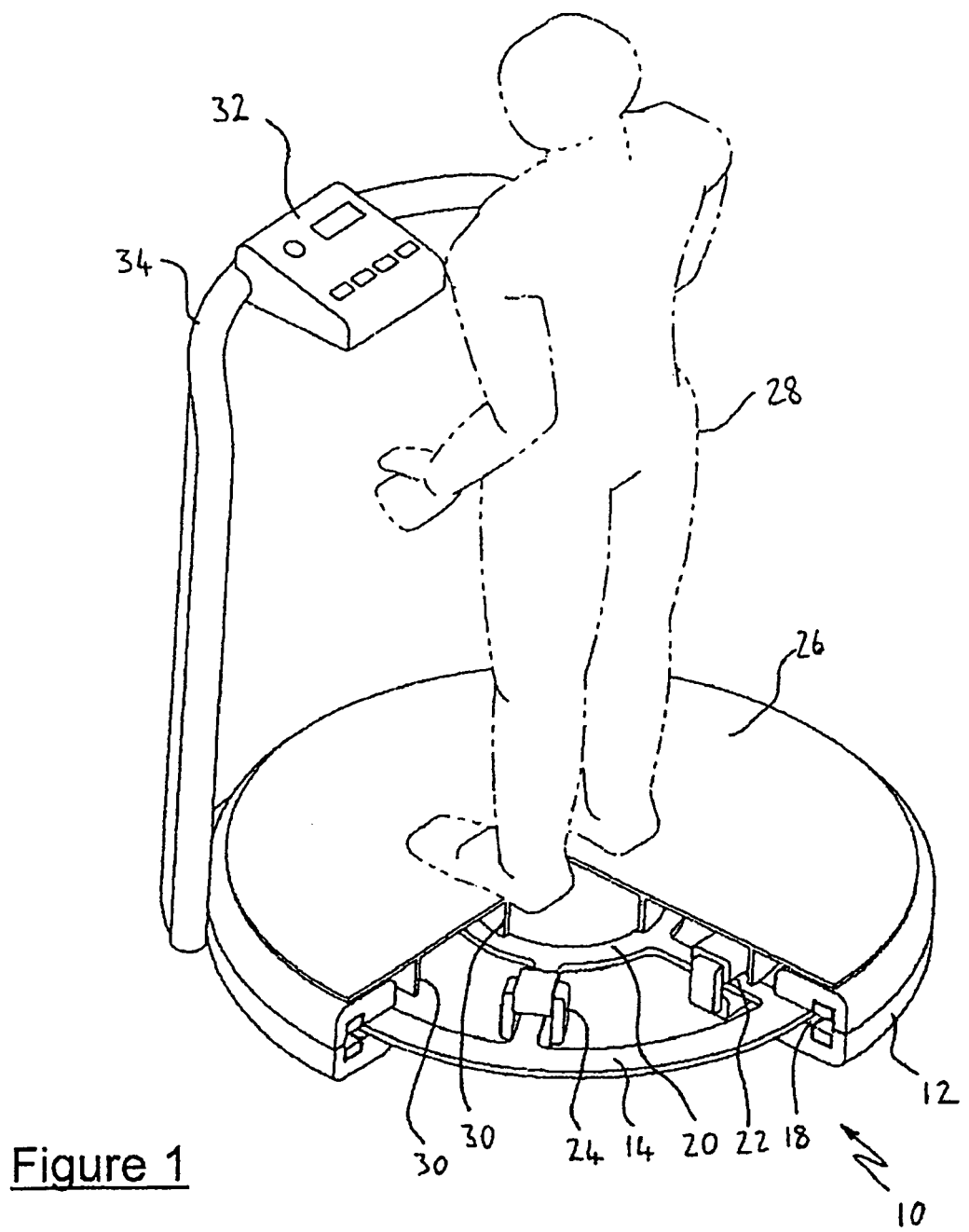
FIG. 1 is a perspective view, partly cut-away, showing apparatus according to a first embodiment used in a method of treating osteoporosis, lymphoedema and for sonoelastography imaging.

The transducer 10 employed in the apparatus and the method of the embodiments has an annular permanent magnet 12 and an armature formed from a disk 14 in the form of a wheel. The permanent magnet 12 is a Cockcroft ring with a C-shaped cross section, having a gap 18 in which the outer circumference of the disk is disposed, and through which lines of magnetic flux flow. The armature has a central hub 20 connected to the disk 14 by six radial arms 22. The arms 22 each have a transformer 24 mounted thereon. The armature is formed of a metal, preferably non-magnetic. By controlling the current flow in each of the transformers 24, current can be induced to flow in the disk 14 (via adjacent arms 22 and the connecting portion of the hub). By inducing current flow in a controlled manner, movement can be induced in the armature, in the x and y axes in the plane of the armature. Furthermore complex two dimensional patterns of movement in the armature can be achieved, through control of current to the six transformers 24. While the embodiments are described with reference to this particular transducer, it should be understood that variations to the construction of the transducer may be made without affecting the operation of the invention. For example, the annular permanent magnet may be segmented in structure, and indeed the construction of the transducer may be that the annulus of the transducer may be divided, perhaps hingeably, for access. The electrical conductive paths may be supplied with electric current by a means other than transformers, and the number of arms 22 and hence transformers or current paths or other means of interacting with the lines of magnetic flux, may be varied.

Particular embodiments can be used in the field of sonoelastography to provide a vibration device capable of inducing at least a two-dimensional motion into tissue during ultrasonic imaging. The vibration source and overall system is provided by an electric motor described in U.S. Pat. No. 6,160,328, the contents of which are incorporated herein by cross-reference. The motor is capable at a minimum of two-dimensional motion with variable frequency and variable amplitude patterns in a common X-Y planar path. One embodiment of the motor is also capable of three-dimensional motion (vibration) with variable frequency and variable amplitude patterns in a common X-Y planar path along with a Z axis oscillations.

In an alternative embodiment, the vibration source and overall system can be provided by an electric motor described in U.S. Pat. No. 6,703,724, the contents of which are also incorporated herein by cross-reference.

Certain embodiments can also be used in a passive method of mechanically loading human bones with a dynamic planar two-dimensional motion for the treatment and prevention of osteoporosis and for fracture healing of bone tissue. In application for treatment of bone, the mechanical strain applied is in the form of flexure with the amplitude being applied substantially perpendicular to the upright skeleton. The person being treated whilst uprightly positioned on the moving platform will endure a sense of vibration radiating up through their body.

As will be described below, the coupling between the vibrating platform and the tissue may be by way of direct contact with the platform, or through an adjustable bellow (foam, air etc) or any other form of size and shape conforming substance, which surrounds the tissue, limb, or body part. Where the tissue, limb, or body part is surrounded, it is most preferred that the bellow is capable of forming a firm fit, so as to maximise the transcutaneous transfer of vibrational energy.

In it simplest two-dimensional form, the apparatus does not utilize a vertical oscillating transducer to impart a compressive stress into the tissue. It utilizes a gentle non-rotating X-Y planetary action to provide radial loads and 360-degree flexure of muscle and tissue. This vibratory motion may be in the form of a planetary action that is set at a given eccentric distance (radius off centre=amplitude) and oscillated at a selectable frequency in the sonic range (below 20 kHz). The two dimensional motion (x y plane) will impart a flexure response to the tissue mass which will, in turn, stimulate the tissue matrix with a full 360 degree moment.

In particular embodiments, the apparatus can provide a passive method of mechanically loading tissue with a dynamic planar two-dimensional motion for the imaging diagnosis of tumours and lesions within the human body. The apparatus can be configured to impart a myriad of strain vibrations at various amplitudes and/or frequencies and/or in various directions. The mechanical stress applied by the apparatus is transferred into strain within the tissue or organ. Applying the stress in two and/or three dimensions simultaneously, results in a better diagnostic interpolation of the tissue condition.

Referring to FIG. 1, the first embodiment shows apparatus used in a method of treating osteoporosis. The apparatus has a contact surface 26 on which a person 28 can stand. The contact surface is formed of a metal or non metal plate supported in insulating manner on circumferential rings 30 on the central hub 20 of the armature, and on the arms 22 adjacent the transformers 24, so that movement induced in the armature is transmitted to the contact surface 26. A microprocessor based controller 32 is mounted on a support frame 34, so that the movement of the armature can be programmed.

Figure 2:
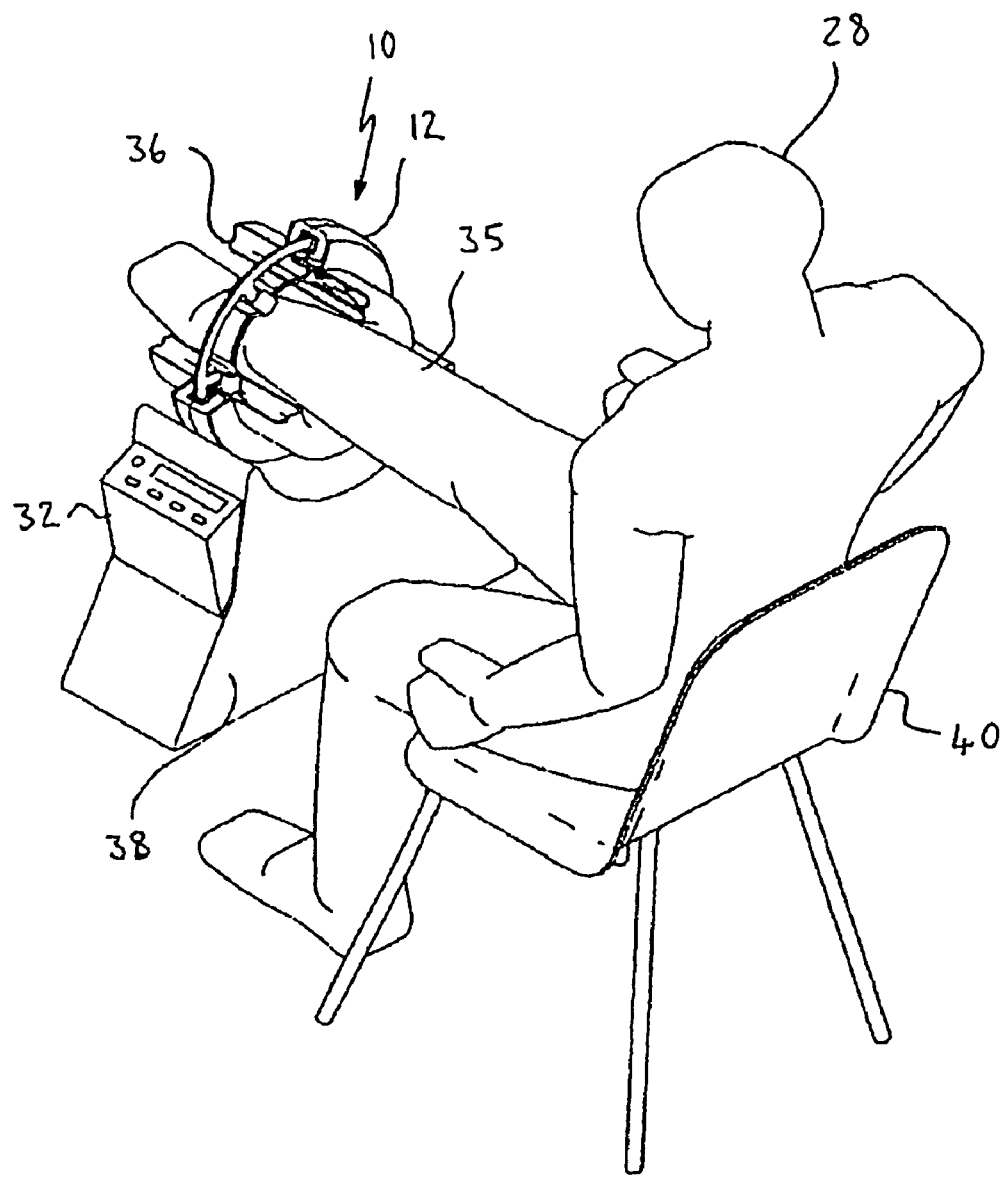
FIG. 2 is a perspective view, partly cut-away, showing apparatus according to a second embodiment used in a method of treating osteoporosis or oedemas, lymphoedema, muscle and tissue conditions, and treatment of bone breakages and fractures, and for sonoelastography imaging.

Referring to FIG. 2, the transducer 10 is mounted with its central axis disposed horizontally, so that a patient 28 can insert their leg 35, through the central hub 20. The apparatus shown in FIG. 2, which is intended to treat osteoporosis or lymphoedema includes the contact surface incorporated in bellows 36 formed of a composite foam rubber with inflatable cells, which is firmly fixed to the central hub 20 of the transducer 10. Once the patient 28 has inserted their limb (in this case leg 35), the bellows 36 is inflated to tightly restrain the limb. The transducer 10 is mounted in a chassis 38, located at an appropriate level so that the patient 28 can be positioned seated in a chair 40. The controller 32 is conveniently located on the chassis 38, so that movement of the transducer can be programmed.

Figure 3:
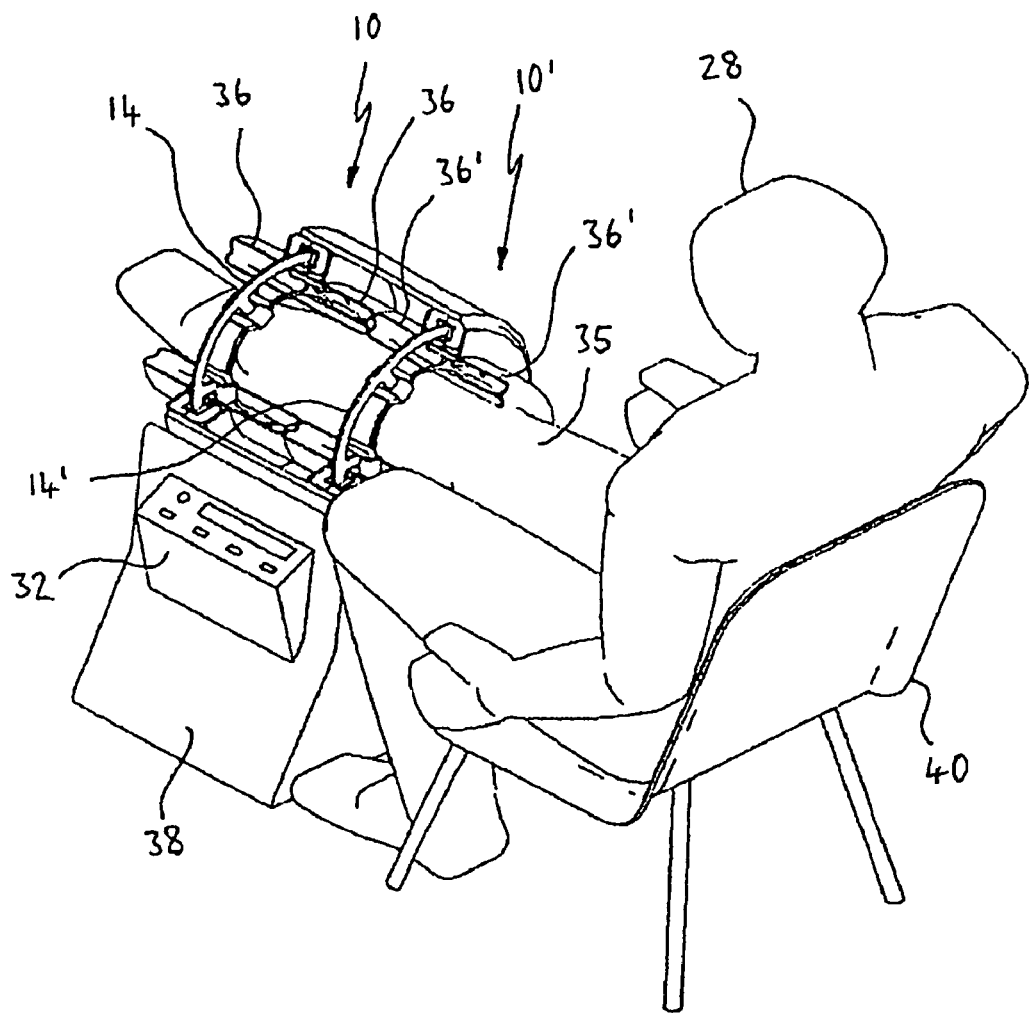
FIG. 3 is a perspective view, partly cut-away, showing apparatus according to a third embodiment used in a method of treating osteoporosis or oedemas, lymphoedema, muscle and tissue conditions, and treatment of bone breakages and fractures, and for sonoelastography imaging.

Referring now to FIG. 3, the third embodiment, also intended for treatment of osteoporosis, oedemas, muscle and tissue conditions and treatment of bone breakage and fractures or lymphoedema is shown. The third embodiment differs from the second embodiment insofar as that there are two identical transducers 10 with bellows 36 located side by side in coaxial manner. This arrangement allows for more complex patterns of vibration to be induced in the patient 28.

Figure 4:
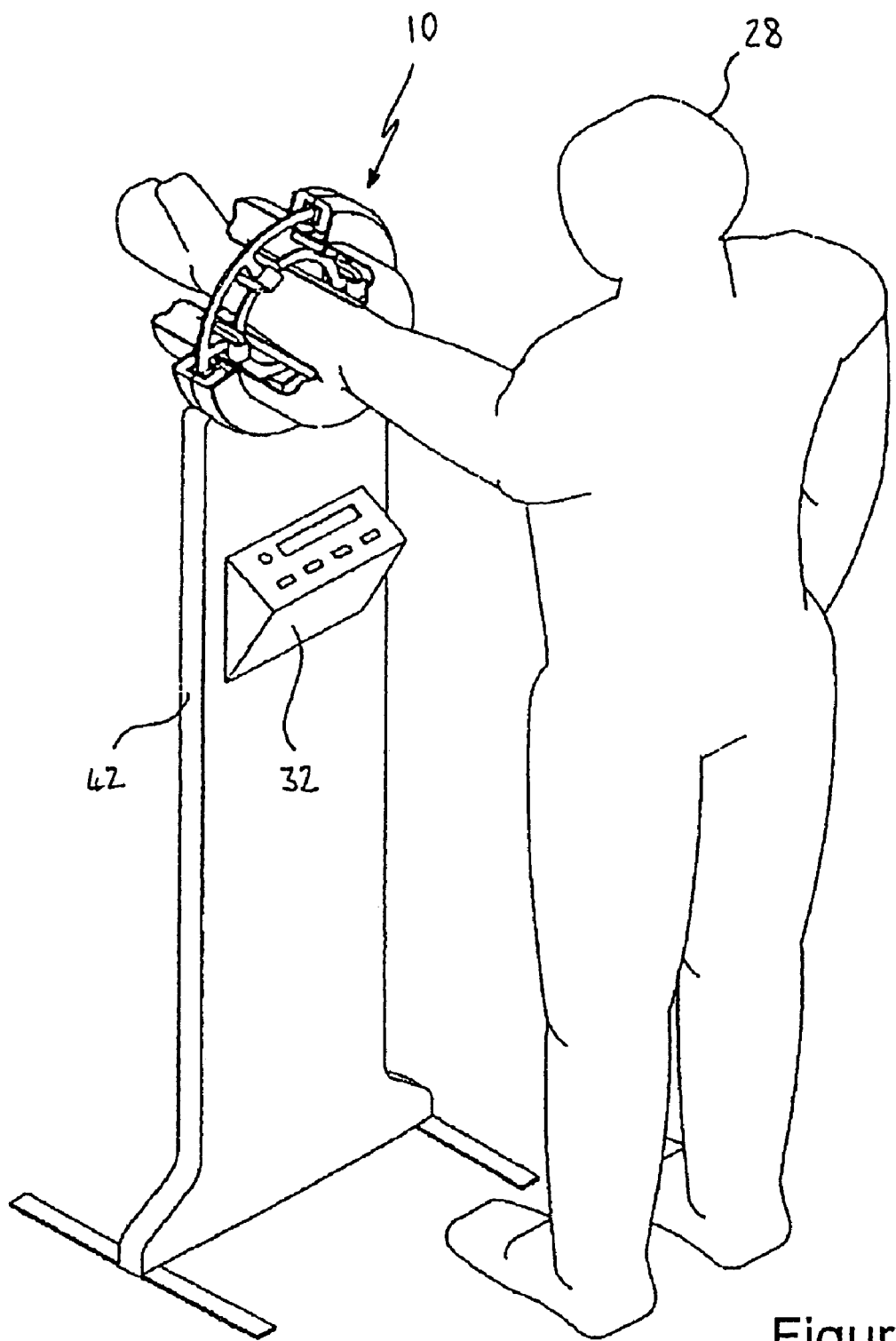
FIG. 4 is a perspective view, partly cut-away, showing apparatus according to a fourth embodiment used in a method of treating osteoporosis or oedemas, lymphoedema, muscle and tissue conditions, and treatment of bone breakages and fractures, and for sonoelastography imaging.

Referring now to FIG. 4, a fourth embodiment is shown for treatment of osteoporosis or lymphoedema, oedemas, muscle and tissue conditions and treatment of bone breakage and fractures and/or sonoelastography imaging. This embodiment differs in that it is mounted in a support frame which disposes a transducer 10 at a suitable height to receive the arm 44 of the patient 28, whilst standing.

Figure 5:
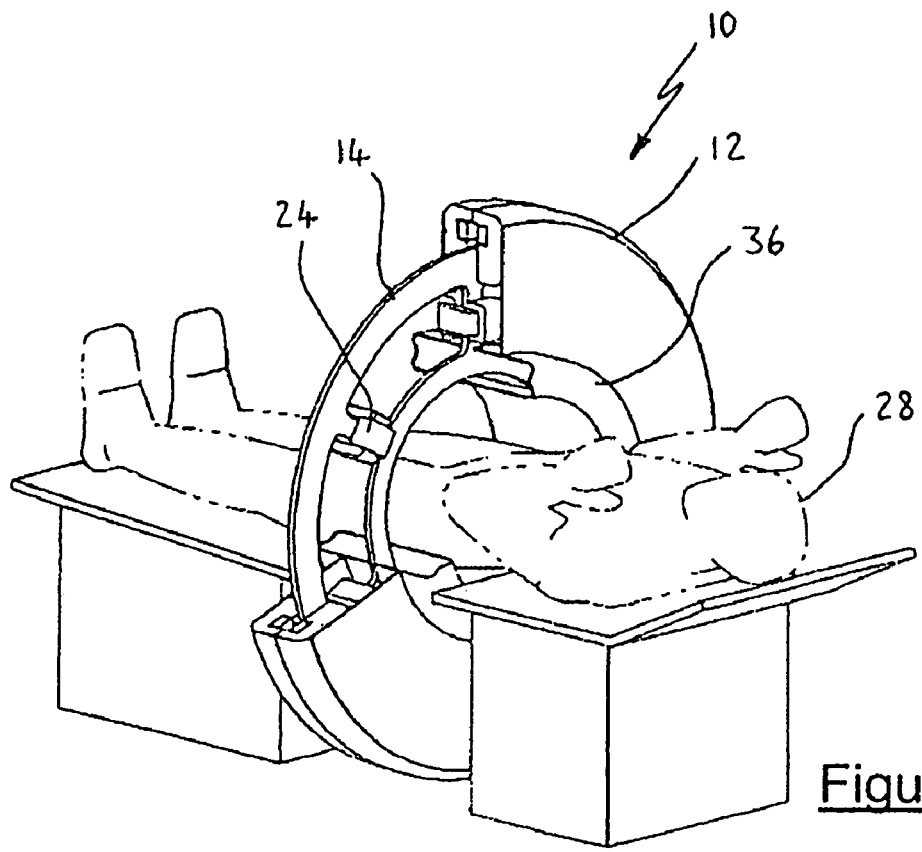
FIG. 5 is a perspective view, partly cut-away, showing apparatus according to a fifth embodiment used in a method of sonoelastographic analysis, treatment of oedemas, lymphoedema, muscle and tissue conditions, and treatment of bone breakages and fractures and osteoporosis.
Figure 6:
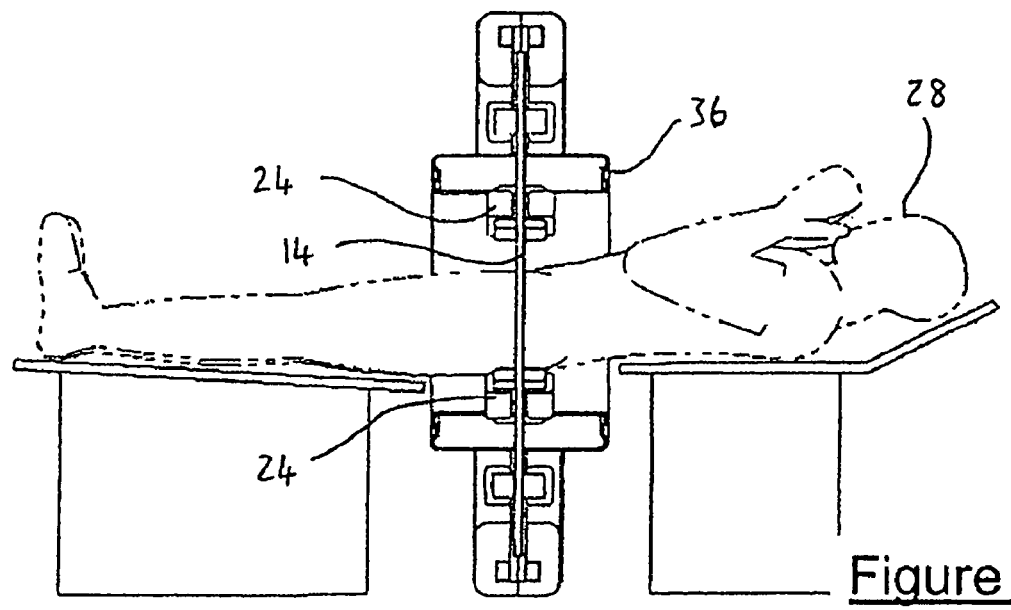
FIG. 6 is a side elevation, partly cut-away, showing apparatus according to the fifth embodiment.

Referring to FIGS. 5 and 6, the fifth embodiment is shown, which is shown being used in sonoelastography to induce vibration through the contact surface in the form of bellows 36, in a patient undergoing imaging by Doppler, ultrasound or magnetic resonance. In use, the patient lies through the bellows 36, resting on the bellows 36 with the region of their anatomy to undergo imaging, in close proximity to the bellows 36. This embodiment is also suitable for the treating of osteoporosis, muscle and tissue conditions or lymphoedema.

It should be noted that each of the embodiments has been shown cut away, so that internal details of the transducers can be seen. It will be understood that the transducer 10 is a circular device, the permanent magnet 12 being a full annulus, and the bellows completely surrounding the limb or body part to be imaged. The transducer can be constructed so as to be dividable, for transport. The embodiments shown in FIGS. 2 to 4 may be constructed so that the transducers can be divided, perhaps hingeably, so that the patient's limb can be easily inserted and removed. In the case of the first embodiment, it should be noted that the contact surface 26 is also a complete disk.

Figure 7:
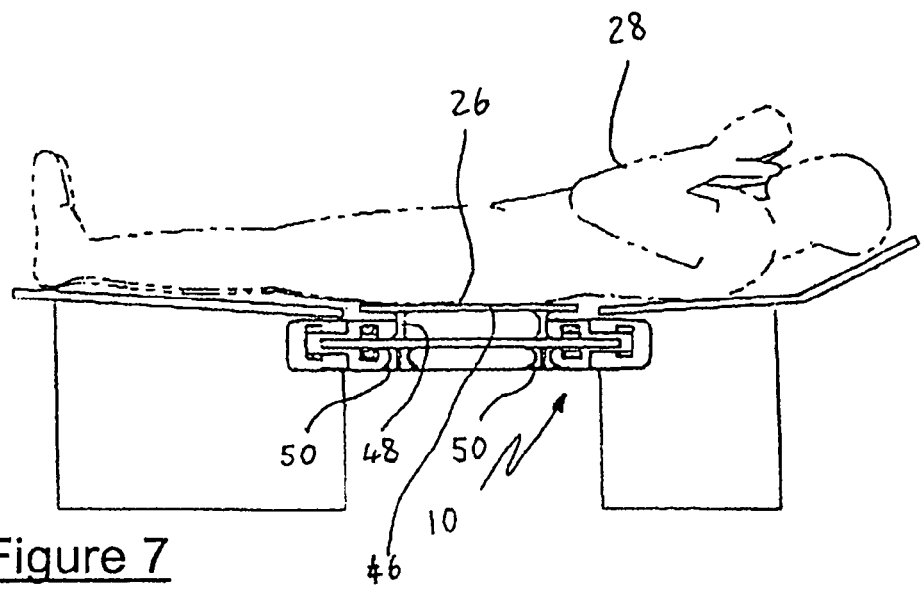
FIG. 7 is a side elevation, partly cut-away, showing apparatus according to a sixth embodiment used in a method of sonoelastographic analysis and treatment of oedemas, lymphoedema, muscle and tissue conditions, and osteoporosis.

The sixth embodiment shown in FIG. 7 is a cross section view showing the transducer 10 lying horizontally. The contact surface 26 is provided as a plate 46 supported on a circumferential ring 48, which rests on the armature. In turn, the armature is supported on flexible rubber mounts 50, which allow for resilient movement of the armature.

Figure 8:
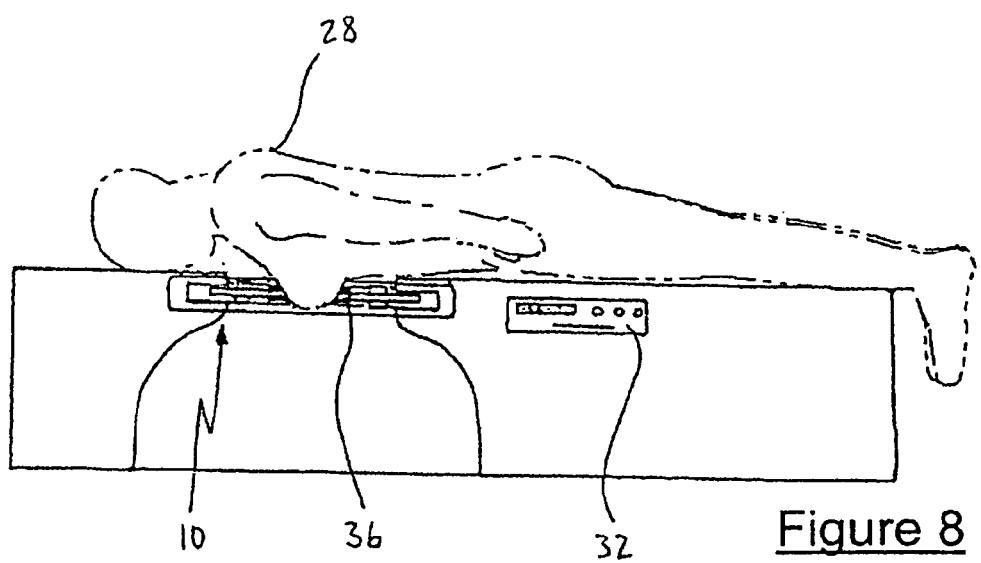
FIG. 8 is a side elevation, partly cut-away, showing apparatus according to a seventh embodiment used in a method of sonoelastographic analysis and treatment of oedemas, lymphoedema, muscle and tissue conditions, and osteoporosis.

Referring to FIG. 8, the seventh embodiment is shown, being a transducer 10 fitted with a bellows 36 having a shape conforming to and capable of receiving (by encircling) a female breast for performing sonoelastographic analysis. The two dimensional vibration induced in the transducer 10 is transcutaneously applied to the tissue region of the breast tissue for tumour diagnosis. In an alternative embodiment, two transducers may be employed simultaneously to compare strain differences between the two breasts.

Sonoelastographic scanning requires the vibration source to be optimised to the correct frequency range to suit the tissue being diagnosed. The embodiment, through the controller, offers this feature by imparting a dynamically tuneable, nonphysiological mechanical stimulation to the tissue in the form of a two-dimensional oscillatory/vibratory motion.

The tissues natural frequency differs by varying degrees for all individuals, with consideration given to the individuals muscle suppleness which is more likely to be a reflection of their age or their disease condition. It is therefore advantageous for broadest application, to have a dynamically variable stimulation device with the capacity to tune the amplitude of vibration and/or the frequency rate whilst the patient is being treated.

In treatment of bone disorders, the mechanical stimulation sets up vibrations in the tissue matrix which will inturn be filtered down to the bone cells. At the cellular level of the bone the signal must be strong enough to apply a flexure strain to the bone so as the bone adaptation process can commence. The bone adaptation process differs by varying degrees for all individuals, with consideration given to their existing bone density and their bone suppleness, which is likely to be a reflection of age or disease. It is therefore necessary to have a dynamically variable stimulation platform with the capacity to tune the amplitude of vibration or the frequency rate whilst the patient is being treated.

The apparatus and methods disclosed herein utilize the knowledge that bones respond to "non-routine loads" far better than customary loads. The mechanical stimuli and therefore the bone adaptation would be more effective if it were site specific due to the differing properties and natural frequencies of various bones. The use of embodiments such as those illustrated in FIGS. 2, 3, 4, and 7 provides for this.

Through the controller 32, there is provided the ability to tune the vibration stimulus to suit the patient by dynamically varying the planetary action without the need to stop the machine whilst the patient is being treated. This can be achieved by dynamically tuning the vibration to the optimal frequency range(s) and amplitude(s) and to change the vibration pattern in a single plane. Typical frequencies envisaged are any frequency from 10 or 20 Hz up to 20 kHz, with displacement of from 0.005 mm or 0.1 mm up to 50 mm.

The vibratory pattern can alternate between a variable "orbit pattern" to a "linear oscillating pattern" and back to an orbital pattern without a pause in the treatment. This tuning can impart an optimised stimulus to more accurately reflect the difference between normal tissue and pathological tissue for various parts of the body whilst being imaged by a Doppler, ultrasound, magnetic resonance or any other imaging device.

The orbital diameter and the linear stroke are completely variable in their amplitudes and can be applied at any desired frequency rate. The linear oscillations can be directed in any radial X-Y component direction in a 360 degree arc, to best direct the strain effect upon a selected lesion area. This multi pattern two-dimensional motion can be infinitely varied to change the strain characteristics received by the tissue to bring about a greater variation in signal feed back to the data correlation equipment.

The motion platform can track a prescribed motion in the form of a "figure of eight" or a "clover leaf", or any "perturbed pattern" that will impart a certain node of stimulation to the tissue or bone. In the treatment of bone disorders, the ability to change the two-dimensional planar/orbital motion changes the strain characteristics which are received by the cell tissue of the bone, and brings about a greater change in bone rebuilding.

Similarly, the controller 32, has the ability to dynamically change the platform's motion pattern in a single plane whilst a patient is lying on an examination table, being treated. The motion platform can alternate between a linear oscillating pattern in a direction of the patient's head and feet (by example) and then switch to a tangential side to side direction or any revolving star like linear pattern around a circle. These features enable the physician to apply the stress in a direction that will apply the desired strain to a tissue to optimise the imaged response. In bone treatment, this allows the physician to direct the dynamic stress where it can apply the desired strain to suit a particular bones orientation. The linear stroke is variable in its amplitude and can be applied at any desired frequency.

The use of the bellow or cuff provides the ability for the device to be located site specific along the body. By cuffing/ encircling around a wrist or arm or leg or the hips or chest or vertebrae, it is ensured that stimulus is received by the bone tissue being targeted for treatment. Hip fractures in particular are very prevalent in the elderly and this invention enables site specific stimulus to that region to aid in reducing the effects of osteoporosis and osteopenia conditions.

Other medical application found for the vibratory transducer is to extend the life of blood platelets in storage beyond the current five day maximum period. With optimal controlled vibration, oxygen transfer to the platelets can be maximized while reducing sheer-force damage, and so maximizing the life of the platelets. Blood platelets are important in treatment following therapy such as chemotherapy.

Another medical application in which the invention finds an application is in the treatment of lymphoedema and, more generally, to the treatment of conditions involving the accumulation of fluid in dependant tissue.

If left untreated the accumulation of fluid in dependant tissue can lead to significant inflammatory problems. In some circumstances the inflammation can have a significant adverse effect on the quality of a person's life and the enjoyment he or she derives from activities associated with everyday living. Ulcers, wounds and lymphoedemas are a few examples.

In the case of lymphoedema the accumulation of lymphatic fluid occurs in the first 0.4 cm to 2 cm of tissue below the skin and may even be much deeper on oedema affected body parts. In more severe cases the lymphatic fluid may inflame the tissue to a thickness of 10 cm or more.

Typically lymphoedema occurs when the lymphatic vessels of the lymphatic system are missing, impaired or damaged, or when the lymph nodes are removed.

Filariasis lymphoedema is a condition where the lymph nodes are impaired by parasitic filarial worms that lodge themselves in the lymphatic system. In 2000 the World Health Organisation estimated that over 120 million people had been affected by the condition with over 40 million of those people being seriously incapacitated and disfigured. The condition is said to exert a heavy social burden including both further complications and social stigmatization.

It is commonly known that radiotherapy and surgeries of the breast, prostate, bladder, and colon place the patient at risk of developing lymphoedema. With cancer patients the most common situations in which lymphoedema results are related to women who have had mastectomy surgery, because of breast cancer, and patients who have had surgery or radiotherapy for cancers of the reproductive system, bowel or prostate. It is estimated that 20-30% of people who have undergone these types of surgery will develop lymphoedema.

Left untreated lymphoedema results in swelling which may in turn lead to serious complications including immobility, painful joints, taut dry skin and subcutaneous tissue becoming fibrotic. Bacteria and fungi may also infect the lymphatic fluid which provides a rich protein food source. This complication is commonly known as lymphangitis and can be life threatening.

U.S. patent application US2003/0171795 to Walmsley and Angel notes some of the more common symptoms of lymphoedema as being limb heaviness, weakness, pain, restricted mobility, burning pains, elevated skin temperature, obvious deformity, social isolation and psychological morbidity.

The current management and treatment of lymphoedema requires continual health professional intervention and patient care. This has a large cost to the community at large while still not providing an effective solution to what can be a debilitating condition.

Treatment methods including breathing exercises, bandaging, massage, small movement and rapid exercise have produced limited results. Some of these methods, such as bandaging, are even prone to significantly worsening the condition of the patient. It would be a great advantage to community, and patients, if the treatment of lymphoedema could be performed more effectively.

The most common of all treatments available is known as "Manual Lymphatic Drainage" (MLD) massage with pressure bandaging. MLD massage is the current world gold standard method and is taught to physiotherapists and occupational therapists throughout the world. With MLD the therapist manipulates the patient with specially learned techniques to draw fluid out of the affected area and into areas where it can be better absorbed by a non-retarded lymphatic network.

In a two-week period of intensive treatment, a patient would typically receive a one hour massage session each morning and afternoon. Each massage session would be followed by wrapping the affected limb in special bandages and keeping it wrapped until the start of the next massage session. At the end of the course of treatment, patients are typically advised to wear a compression garment covering the limb at all times during the day and, also, to bandage the limb or wear a special overnight type of compression garment every night. This is very cumbersome and inconvenient for the patient.

Because the lymphatic vessels are fragile and easily damaged, MLD can generate fibrotic scar tissue. In some cases the pressure also forms holes through the skin. This allows for bacteria to enter and cause infection. In addition to some cases of infection being life threatening, the movement of lymphatic fluid, during massage, to another region, such as the groin, can cause that area to become lymphoedematous. For these reasons MLD is far from an effective method of draining lymphatic fluid. Other even less effective treatment techniques include compression pumps with inflatable sleeves and low level laser therapy.

Practitioners typically prescribe a regime of patient care comprising: (i) washing and moisturising the skin to avoid infection; (ii) protecting the skin from cuts, scratches, inset bites, knocks and sunburn; (iii) using an electric razor; (iv) applying a disinfectant and contacting a doctor if injury occurs; (v) avoiding wearing watches, rings and bracelets, which in some circumstances could damage the skin; (vi) avoiding standing still for long periods of time; (vii) ensuring that the limb is exercised normally; and (viii) avoiding any pushing or lifting of heavy objects. Even when adhering to such a regime of patient care, recurrent inflammatory episodes (DLA) are a common complication.

A method of vibration for the treatment of lymphoedema is disclosed in US2004/0077978 to Nelson et al. This method and methods of vibration that have been available to date are not particularly effective.

Figure 9:
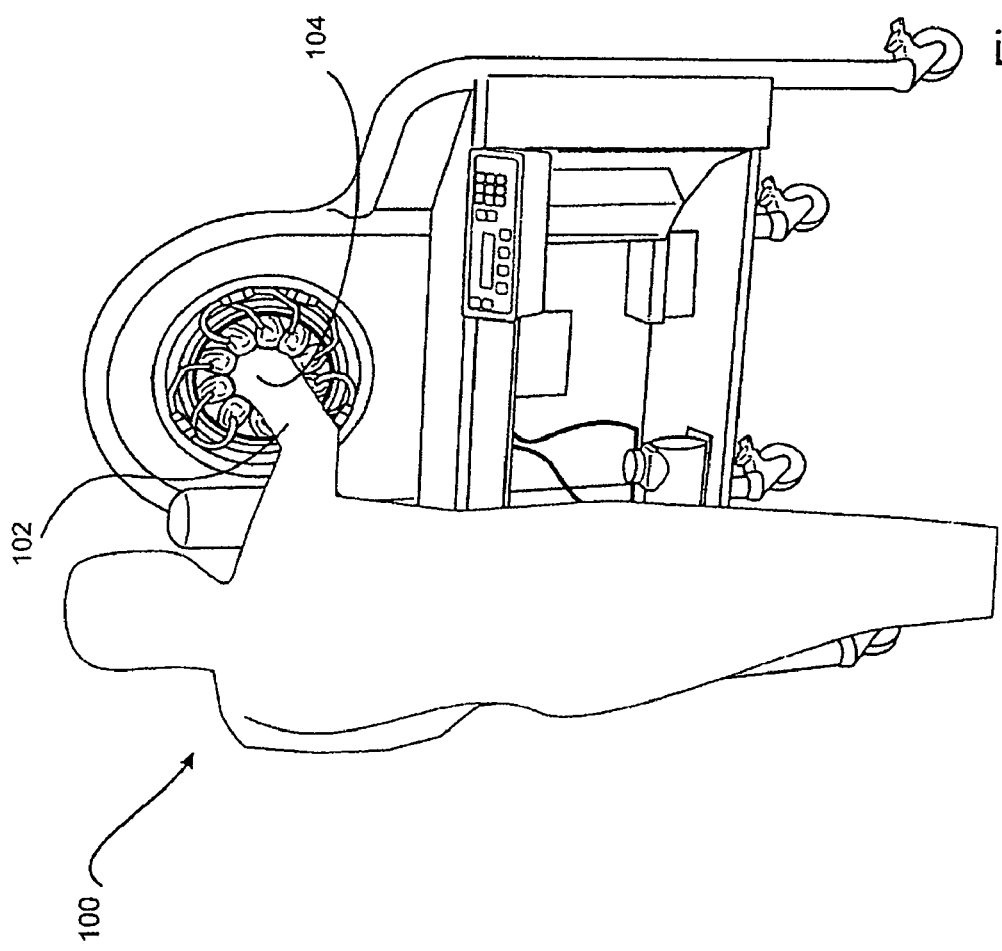
FIG. 9 is a perspective view, partly cut away, of an apparatus treating a patient according to a first embodiment.

Referring now to FIG. 9 there is shown an patient 100 being treated with an apparatus 101 according to a first embodiment. The patient 100 has lymphoedema in his left arm 102. The arm 102 and the tissue affected by the lymphoedema is stimulated with a complex pressure stimulus that varies around the arm 102 in accordance with a particular pressure variation pattern. The pressure variation pattern varies substantially perpendicularly to the length of the arm 102.

As a result of the pressure variation a relatively rapid movement of interstitial fluid moves from the affected arm 102 into the lymphatic system of the patient 100.

Whilst various forms of pressure pattern such as a symmetrical five pointed star (described below) are encompassed by embodiments of the present invention, to provide the advantages thereof, the stimulus in each embodiment stimulates the epidermis, dermis and subcutaneous layers of the affected tissue such that there is a relatively rapid movement of interstitial fluid in the affected tissue into the lymphatic system. With the method of the present embodiment employing a symmetrical 20 point star pattern a movement of 80 milliliters over a seven minute treatment session is able to be achieved in the circumstances of a patient having relatively mild case of lymphoedema in their arm. This is a significant improvement over present methods of moving lymphatic fluid out of interstitial tissue back into what is otherwise a depressed lymphatic system.

The present embodiment is able to achieve such a movement of fluid without appreciably putting areas of unaffected tissue at risk. This is a significant advantage given that with MLD and other common techniques the fluid can cause areas adjacent to the affected tissue to become lymphoedematous.

In the lymphatic system lymphatics can be categorized as initial and collecting lymphatics. Collecting lymphatics are provided with smooth muscle intima and contain lymphangions. The lymphangions are formed in series and are separated from each other by a valve.

Whilst in no way being limited to any particular theory, and noting that the operation of the lymphatic system has not been conclusively determined, it is thought that present embodiment is able to achieve the above results by setting up a special induced vibration of the contractile lymphangions of the lymphatic system.

Gerli, Ibba and Frishecelli in their article entitled "Morphometric analysis of elastic fibres in human skin lymphatic capillaries, *Lymphoglogy*, 1989 Dec; 22(4), 167-72 explained that the elastic fibre network commonly seen adjacent to collecting lymphatics is orientated substantially longitudinally to the lymphatic vessel wall.

The anchoring structure of microbrils of lymphatics capillaries is discussed by the same authors in their article entitled "Ultrastructural cytochemistry of anchoring filaments of human lymphatic capillaries and their relation to elastic fibres, *Lymphoglogy*, 1991 Sep; 24(3), 105-12.

Very basically the initial lymphatics provide the first point of entry and collection for the lymphatic fluid. They provide a pliable structure of endothelial cell gates or intercellular clefts which are driven by pressure gradients across the walls of the structure.

It is considered that if the interstitial fluid can gain entry into the initial lymphatics through the cell gates it will fill and stimulate the flow of interstitial fluid on a one way journey past the first value set into the start of the collecting lymphatics. Expansion and contraction of the initial lymphatics will commence once the peristaltic pumping process of the lymphatic system has started.

With the present embodiment it is thought that the method stimulates the anchoring filaments of the initial lymphatics in a concerted manner so as to influence the opening of the endothelial cell gates of the initial lymphatics, thereby causing the relatively rapid movement of interstitial fluid in the affected tissue into the lymphatic system. This method of stimulating the lymphatic system has not been previously performed.

The process of dilatation of the initial lymphatics aids the absorption of the interstitial fluid in through the endothelial cell gates to fill the lymphatic lumen and signal the start of the pumping procedure. The dilation of the initial lymphatics causes the lymphatic pressure to gradually decrease in the lymphatic lumen below the interstitial fluid in the tissue, causing the unattached endothelial cells to open inward allowing for fluid entry into the initial lymphatics. As the lumen fills the fluid pressure inside increases, effectively closing off the endothelial cell gates to stop reflux flow back into the tissue spaces. This is the same effect of the hydrostatic or osmotic pressure gradient for fluid lymphatic transfer.

The anchoring filaments can be generally viewed as semi-elastic fibres that hold the initial lymphatics in place and attach to the many individual endothelial cell walls of the initial lymphatics. The anchoring filaments cause flexing on the endothelial cells and aid the opening and closing of the intercellular junctions so that proteins, fluids and small molecules can move into the initial lymphatics and be taken away.

Once the interstitial fluid has entered and filled the initial lymphatics it triggers the next pulsatile muscle chamber to contract, moving what is now called the lymph fluid along a network of one-way pulsatile collectors to the lymph node junctions throughout the body.

In terms of what can be physically observed, the embodiment induces a ripple effect along the arm of the patient 100. The ripple effect is induced along the surface of the patient's skin away from the stimulus and extends at least all the way up to the shoulder of the patient 100. Whilst the stimulus is applied to a relatively thin band around the forearm 104 of arm 102, the method as evidenced by the ripple effect operates over the length of the arm 102.

While some prior art methods such as that described in US2004/0077978 entitled "Leg Ulcer, Lymphoedema and DVT Vibratory Treatment and Device", to Nelson et al, do exist, the pressure variations applied in these methods comprise simple varying sinusoids applied in orthogonal x, y and z directions through a central origin. With the prior art the path followed by the vibration in the x and y plane is circular due to the centrifugal motion of the rotating counterweight. There is no complex pressure stimulus nor a directional stimulation change. The pressure variations described in US2004/0077978 are not sufficient to cause the improvement of the present embodiment. Among other things, neither do they generate a ripple effect as encompassed by the present embodiment.

The pressure stimulus applied by the present embodiment departs from simple circular sinusoidal motion and in this sense disturbs ordinary motion and is perturbed. The complexity of the pressure stimulus is evident in different applicable patterns such as clover leafs, five pointed stars, figures of eight and so on. Pointed stars patterns have directional stimulation change at the point of the star that is particularly advantageous for inducing a relatively rapid movement of interstitial fluid in affected tissue into the lymphatic system.

Figure 10:
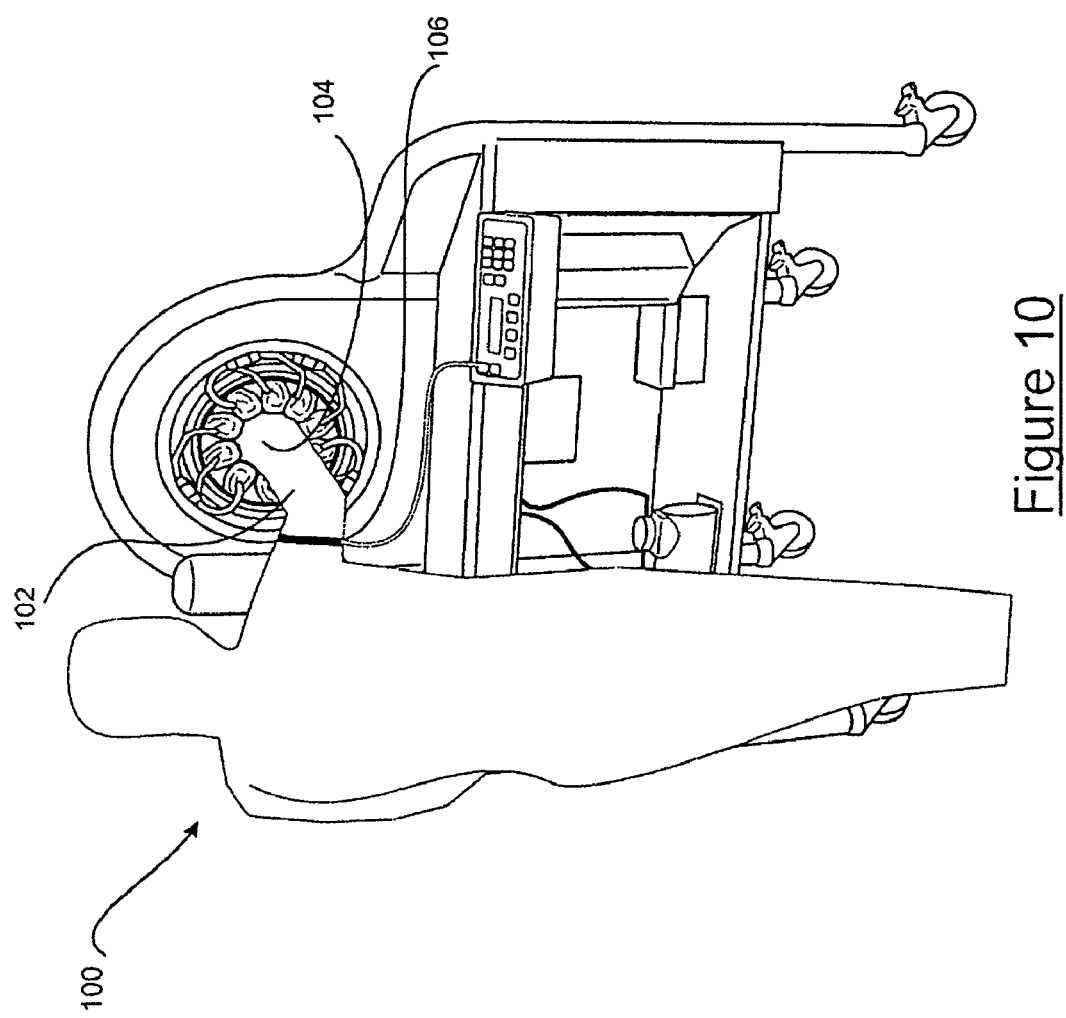
FIG. 10 is a front view of the apparatus shown in FIG. 1, the apparatus being coupled to a sensor whereby the arrangement, in combination, is in accordance with a second embodiment.

The embodiment shown in FIG. 10 includes a receiver 106 for receiving response information from the patient 100 and control means for adjusting the rate and intensity of the stimulus according to the response information and predetermined criteria. The predetermined criteria is formulated for ensuring that the movement of interstitial fluid into the lymphatic system is controlled so as not to be adverse to the patient. It is envisaged that in some circumstances the movement of fluid may so great as to cause complications to the general health of the patient.

The receiver 106 is also used to detect the extent of the ripple along the arm 102 of the patient. By detecting the extent of the ripple, including possibly both its magnitude and direction, the apparatus 100 is able to determine and select a resonant frequency of the layers of tissue of the arm 102 and alter the stimulus so as to increase or decrease the pressure variations at that frequency to assist with maximizing the fluid transfer for that patient.

Figure 11:
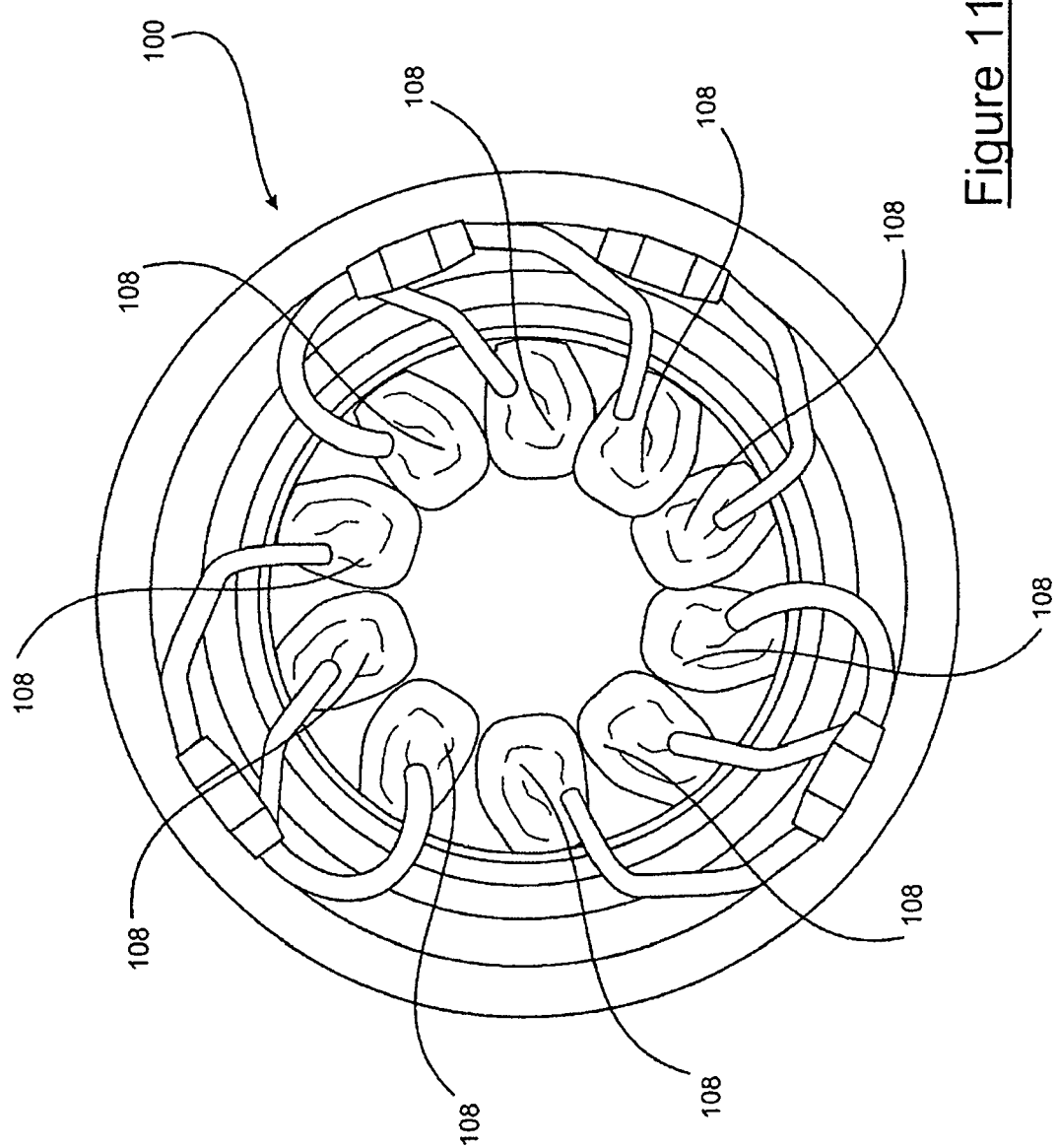
FIG. 11 is a front view of the apparatus shown in FIGS. 1 and 2.
Figure 12:
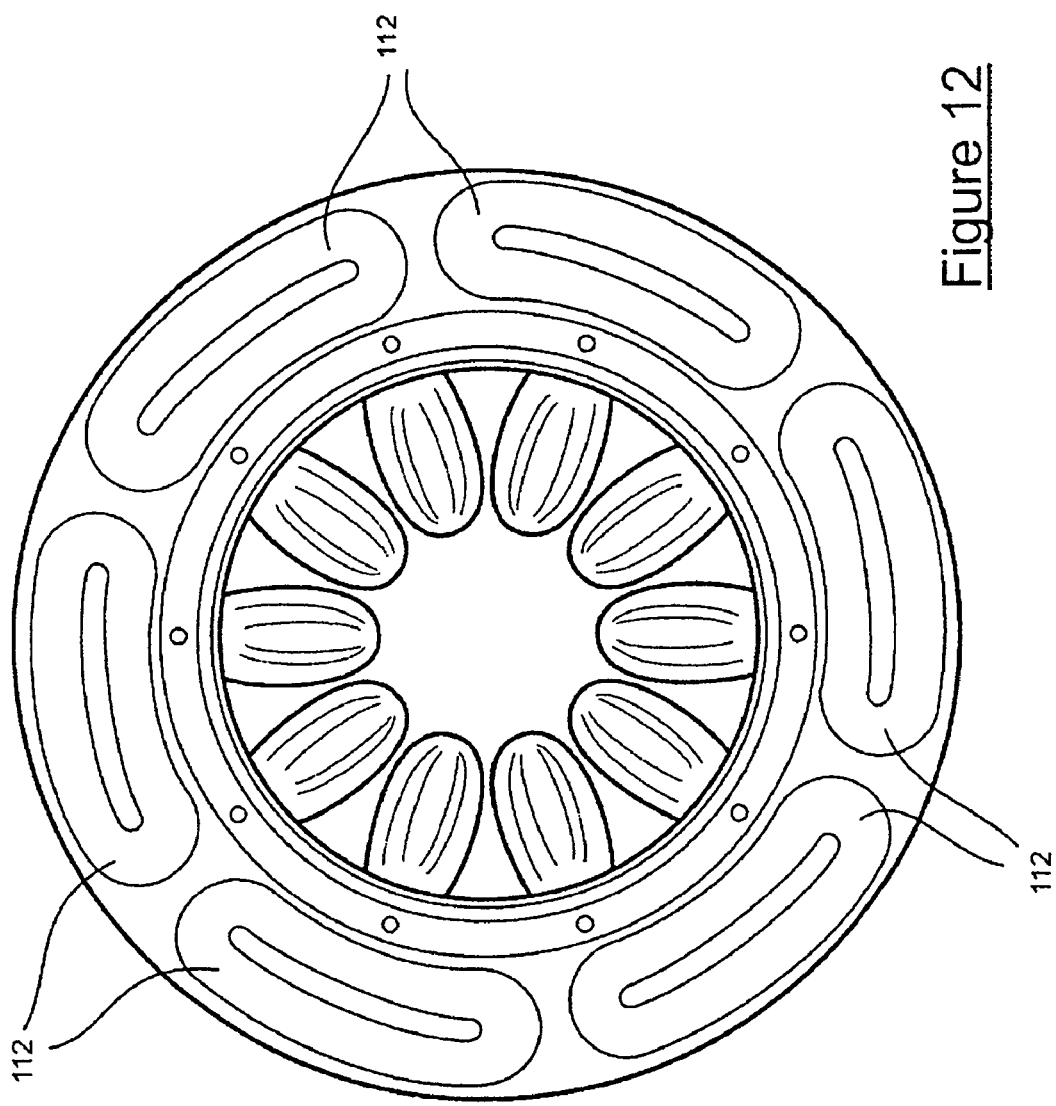
FIG. 12 is a perspective view of an armature used in the apparatus shown in FIG. 1, 2 and 3.

With reference to FIG. 11 in particular, it can be seen that the apparatus 100 includes a cuff structure in the form ten compartments 108 that are adapted to surround and closely conform to the arm 102 of the patient 100. The compartments 108 are connected together by a porting system to ensure that the compartments 108 are substantially, in the sense of at least partially, isolated from each other when pressurized with working fluid. In this embodiment water provides a suitable working fluid. The water is held in a reservoir that is advantageously pressurized by air from a provided pressure source. By virtue of the working fluid being water there is provided a good transfer medium for vibration. In alternate arrangements varying density foams could also be used as could any conforming gas or material.

When pressurized, the compartments provide a contact surface with a surface area for frictionally coupling to a corresponding surface area of the patient 100, namely the forearm 104. The corresponding surface area extends about the arm 102 of the patient 100. The compartments 108 may be viewed as a particular and advantageous form of a bellows arrangement.

Each of the compartments 108 is connected to a rigid circular boss attached to an armature 110 having a plurality of electrical coils 112. The compartments 108 are filled with the working fluid. While not shown in the drawings in particularly preferred arrangements the boss is provided in the form of a collapsible iris having segmented parts that allow for variable size adjustment. The electrical coils are placed in a magnetic field and the current is applied to the coils such that the armature 110 is able to follow a pattern of movement and provide a similar pressure variation pattern to the arm 102. By having individual substantially isolated compartments 108, each compartment 108 is able to apply a relatively independent pressure at particular locations around the arm 102.

As a consequence of basic geometry, diametrically opposite compartments 108 move in similar directions thereby applying a consequential pressure variation around the axial direction of the arm. This has advantageous benefits for providing ripple effect and stimulation of the anchoring filaments in multiple directions without potentially damaging compression of the tissue from opposing sides.

While an armature having six degrees of freedom (pitch, yaw, roll and three translational degrees of freedom) or less may be used, the illustrated armature 110 has two degrees of translational freedom in the x, and y directions. An armature that is able to stimulate the arm in multiple modes of operation, that is dimensions of movement is readily constructed. U.S. Pat. No. 6,703,724 entitled "Electric Machine" provides guidance as to how the electrical coils 112 are employed to form a complete motor that can provide the required motion.

Figure 13:
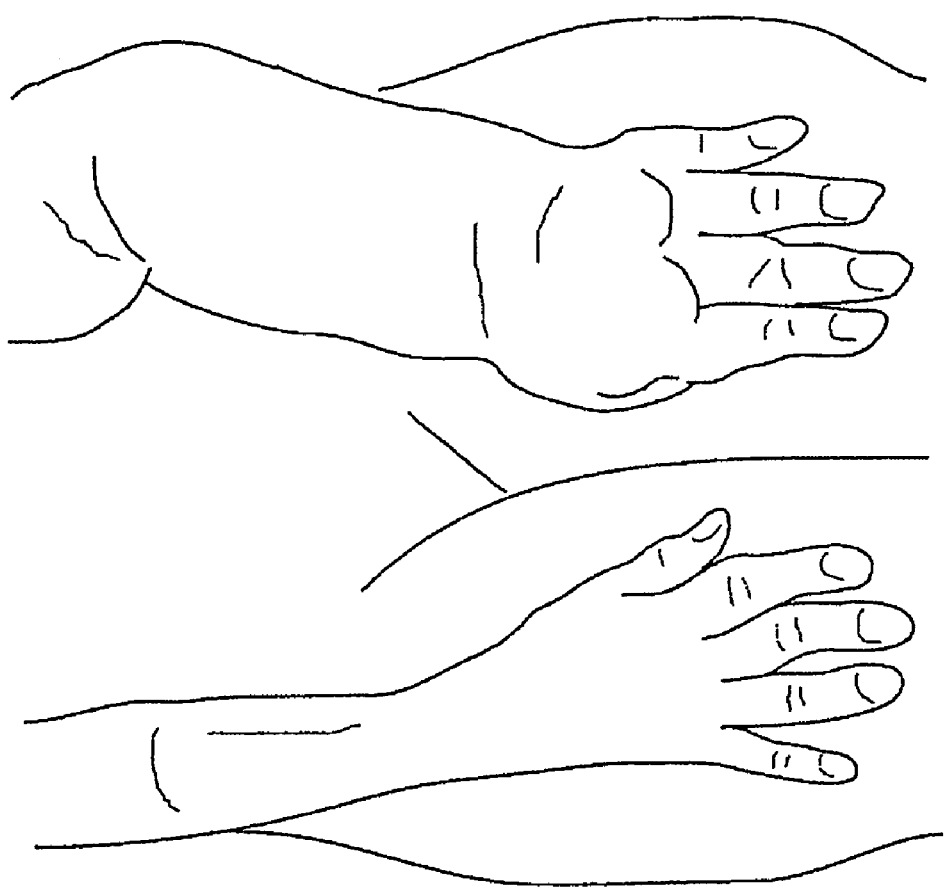
FIG. 13 is a line drawing of a photograph showing a woman having lymphoedema in her left arm.

FIG. 13 is a line drawing taken from a photograph of a woman having lymphoedema in her left arm. The difference in the sizes of her arms is real.

With the use of the present method the woman will not have to attend MLD therapy sessions which as noted typically span over two weeks. A course of the present method is envisaged to be applied as a home treatment or in a specialised clinic and may require, depending on the particular situation, at least two treatments over a two week period, each treatment taking about 15 minutes each without the subsequent requirement of pressure bandaging. The effectiveness of the present invention and the lack of potential complications provides a significant breakthrough.

Figure 14:
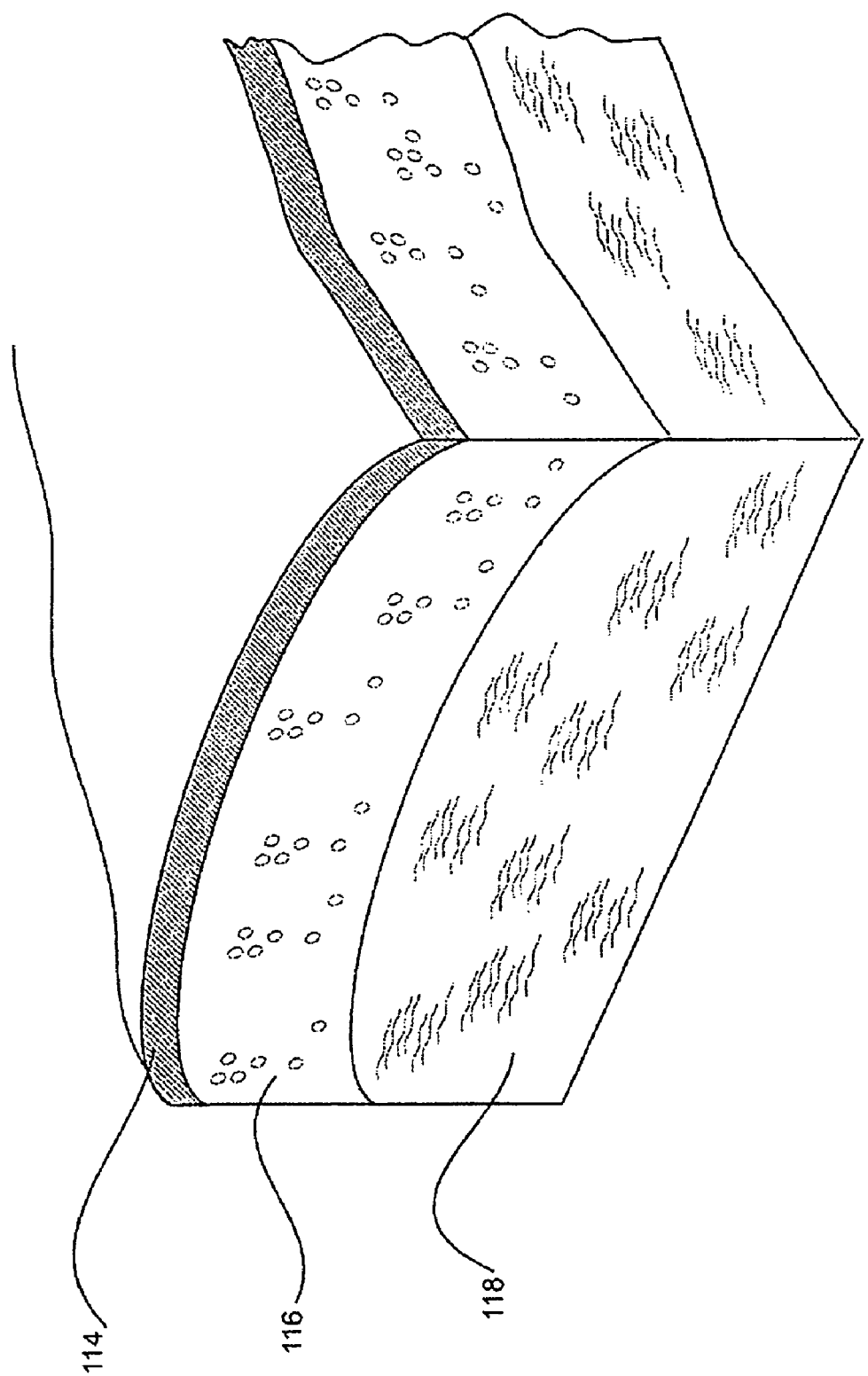
FIG. 14 is a schematic perspective view, in section, of a layer of skin.

A layer of skin is shown in FIG. 14 for completeness. The first layer is known as the epidermis 114. The epidermis 114 is translucent. The second layer is known as the dermis 116. The dermis 116 contains blood vessels, nerves, hair roots, lymphatics and sweat glands. The third layer is known as the subcutaneous layer 118. The subcutaneous layer 118 contains larger blood vessels and nerves and is primarily made up of fat-filled cells called adipose cells. The third layer has large lymphatic supplies. There are abundant publications on the make up of the skin and the reader is referred thereto for a complete analysis.

Figure 15:
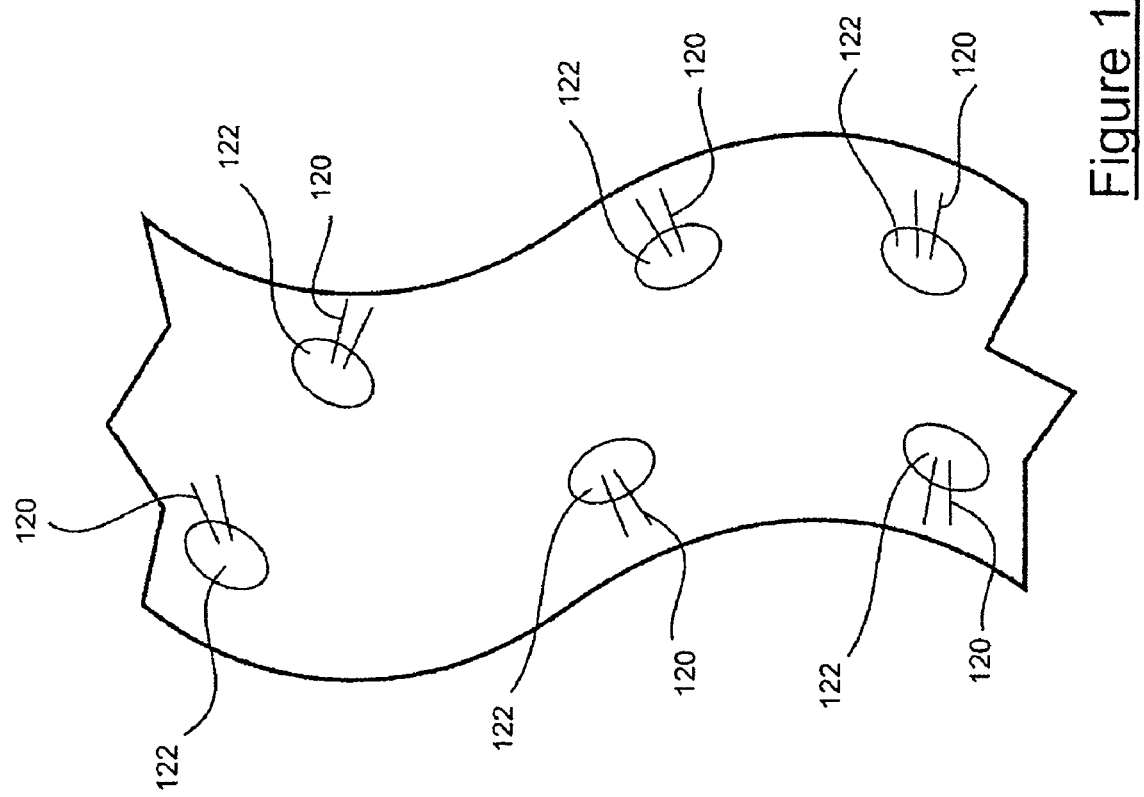
FIG. 15 is a schematic view of a lymphatic in the skin shown in FIG. 7, the lymphatic being stimulated according to a third embodiment of the invention.

A number of anchoring filaments 120 in the subcutaneous layer 118 are shown in FIG. 15. The anchoring filaments 120 are connected to endothelial cell gates 122 as previously described. The anchoring filaments 120 are stimulated by the complex pressure variations to cause the relatively rapid movement of interstitial fluid in the affected tissue, into the lymphatic system.

Figure 16:
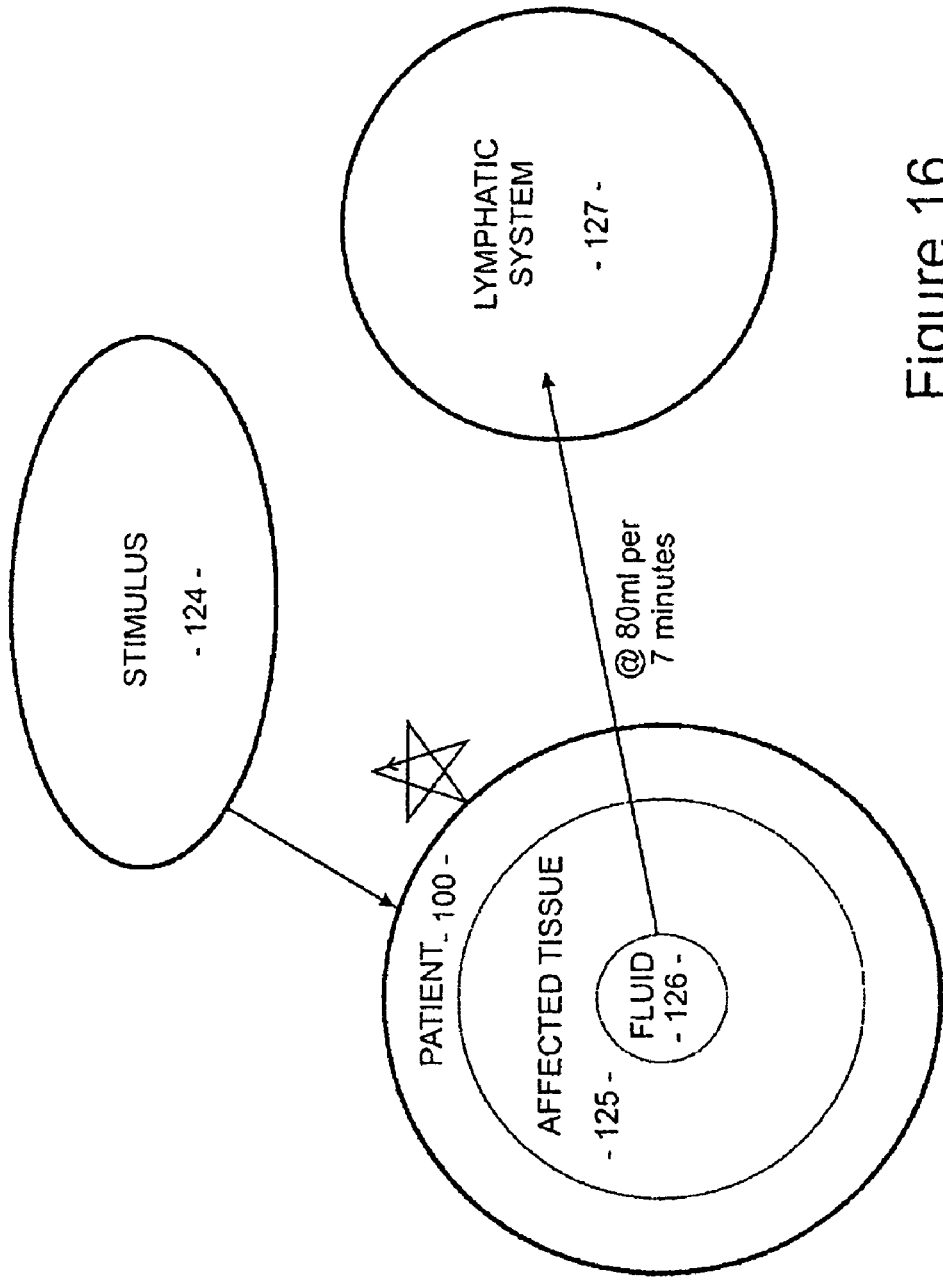
FIG. 16 is a schematic view of the embodiment applied in FIG. 7.

FIG. 16 illustrates an embodiment in schematic form that operates on a number of lymphatics as shown in FIG. 15. A patient 100 is subject to a complex pressure stimulus 124 operating in multiple directions. The stimulus 124 stimulates the affected tissue 125 of the patient 100 such that there is a relatively rapid movement of interstitial fluid 126 in the affected tissue into the lymphatic system 127. Depending on the circumstances and on the particular method of complex pressure stimulus applied, about 80 milliliters of fluid may be moved in seven minutes.

Figure 17:
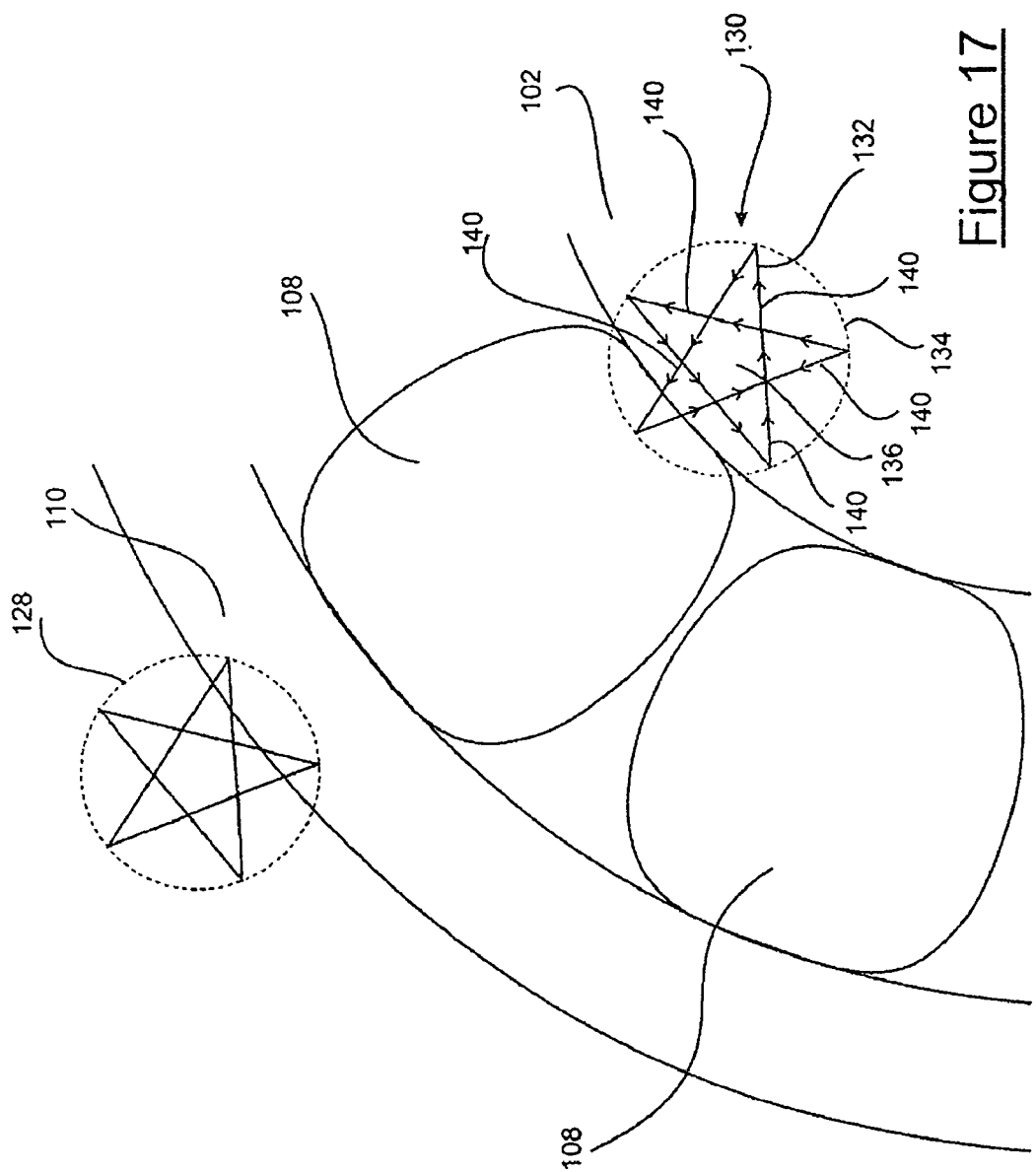
FIG. 17 is a schematic front view of part of an apparatus operating according to the embodiment schematically shown in FIG. 8.

The particular pressure pattern used is shown in detail in FIG. 17. A member 110 surrounds the arm 102 and is translated in accordance with a two dimensional pattern of movement 128.

By virtue of the compartments 108 being connected to the member 110 the translation of the member 110 creates the pressure variations in the pressure applied to the arm 102 of the patient. The pressure variations are generally designated 130. As is apparent the pressure variations 130 are directed substantially along a path 132 that is arranged within a circular area 134.

Furthermore the path 132 substantially avoids travelling back and forth over a central region 136 of the area 134. The central region 136 is bounded by a pentagon formed by the path 134. This is thought to set up particularly beneficial pressure fluctuations operating to have the effect of causing relatively high fluid movement in the lymphatic system.

The pressure variations are applied by the compartments 108 in multiple directions substantially normal to the axial length of the arm 102 by virtue of the circular area 134 being arranged substantially perpendicular to the length of the arm 102.

As can be seen from FIG. 17 the path 132 comprises five path elements 140 arranged end to end, with each end positioned to lie substantially on the circular area 134, so that the five path elements 140 form a continuous and substantially symmetrical five-pointed star.

The pressure in the compartments 108 is maintained so that the layers of tissue are stimulated at magnitude of about 2 mm, peak to peak, at a frequency of about 35 Hz. The frequency and amplitude are dynamically varied according to the condition of the patient 100, and as the effects of resonance are observed. The frequency of 35 Hz is measured in terms of the time taken to complete a full cycle of the pattern along path 132, being 35 full cycles per second. The velocity of any one path element of the whole path is at a rate of one fifth of the full pattern rate, that is the whole pressure variation is one fifth of this amount.

A linear oscillator travelling a distance of 0.5 meters each stroke at 1 Hz will have a velocity of 1000 mm per second. Comparatively a five pointed star travel path of the embodiment operating at 1 Hz within a confining circle of 0.5 m in diameter will have a velocity of approximately 2380 mm per second with a cord length of about 475 mm. So to maintain the same frequency an embodiment would have to travel 2.4 times faster than the linear oscillator. To apply the same velocity to a persons arm, in comparison to a 1 Hz liner oscillator, the embodiment would have to operate at a frequency of 0.42 Hz.

Figure 18:
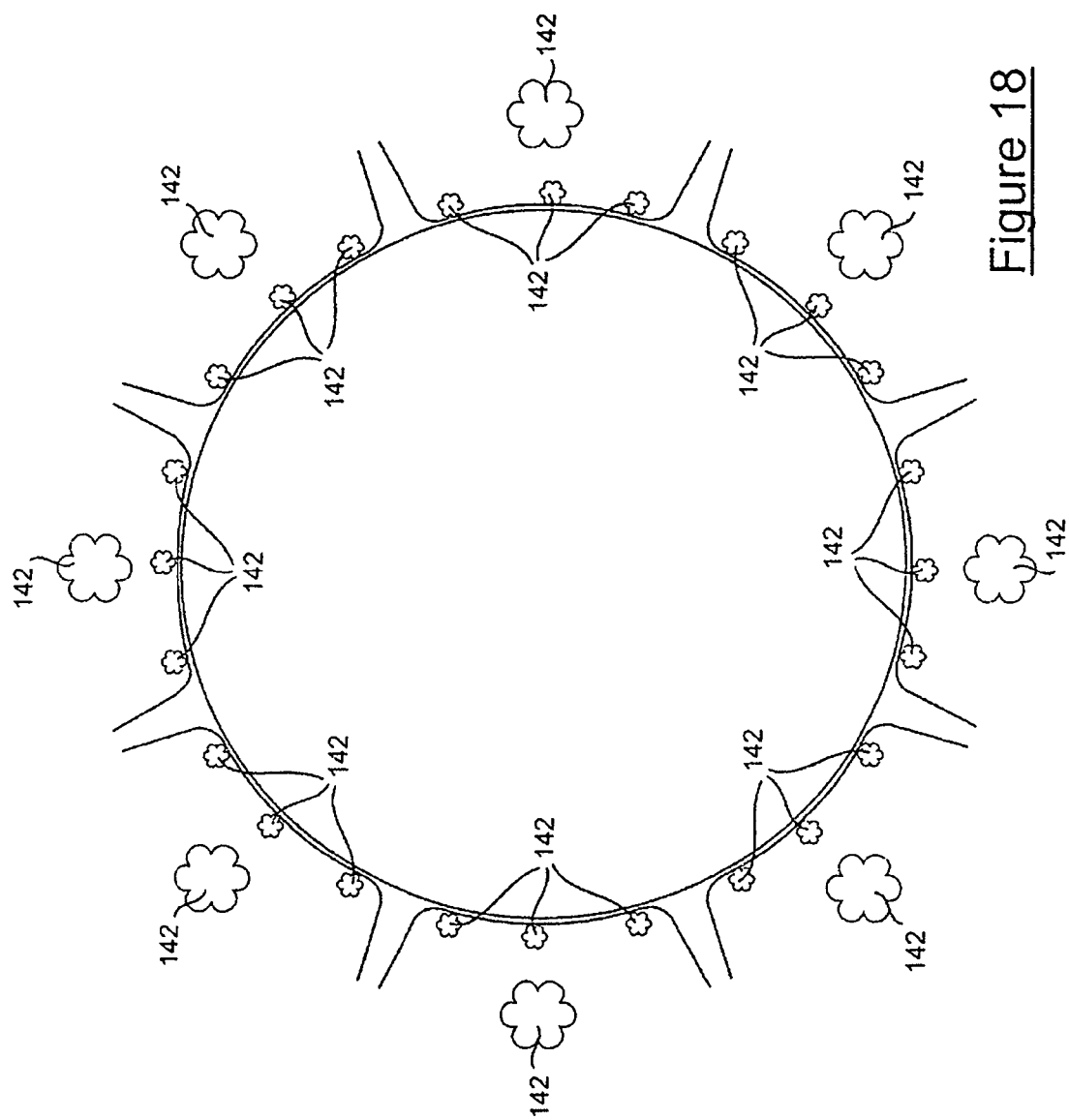
FIG. 18 is a view of a path used in a method according to a fourth embodiment.
Figure 20:
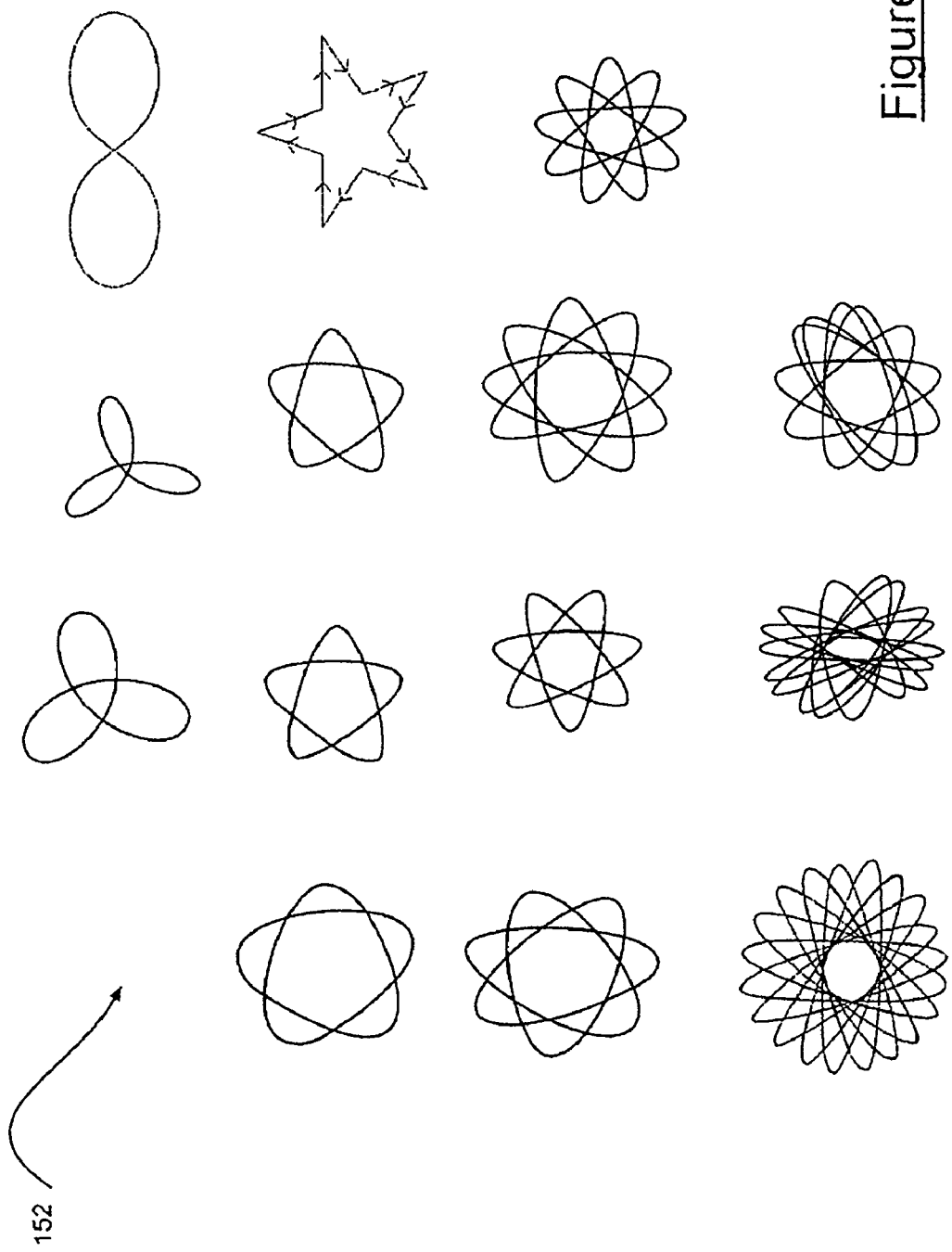
FIG. 20 is a schematic view of various paths for use with embodiments disclosed herein.

An alternate six leafed clover path 142 is shown in FIG. 18. The use of variable leafed clover paths is obviously within the scope of the present invention as are each of the paths 152 shown in FIG. 20. The paths 152 are complex and are not spherical, cycloidal or linear. They also follow a path of at least three non-colinear points for each cycle of stimulation. Various other paths fall within the scope of the invention.

In a particular embodiment producing notable benefits, the path 132 comprises twenty path elements arranged end to end, with each end positioned to lie substantially on a circle such that the twenty path elements form a continuous and substantially symmetrical twenty-pointed star. Each path element of the pointed star is slightly curved at its ends so that the star is formed with rounded points. As would be apparent the invention comprehends any star pattern, or any other pattern, that is non-symmetrical in its displaced path.

Figure 21:
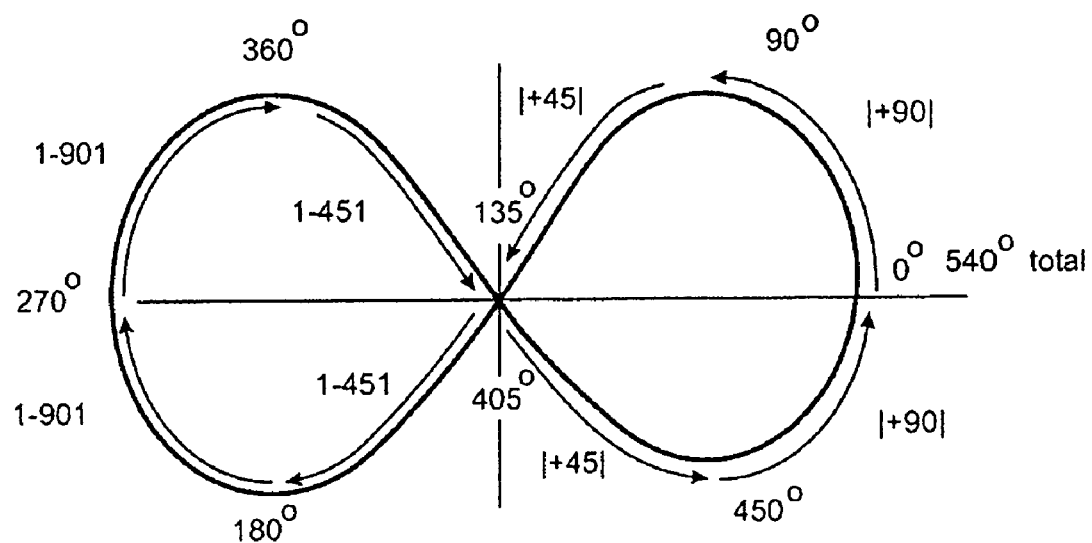
FIGS. 21 and 22 are schematic views of various paths having a particular form according to certain embodiments.
Figure 22:
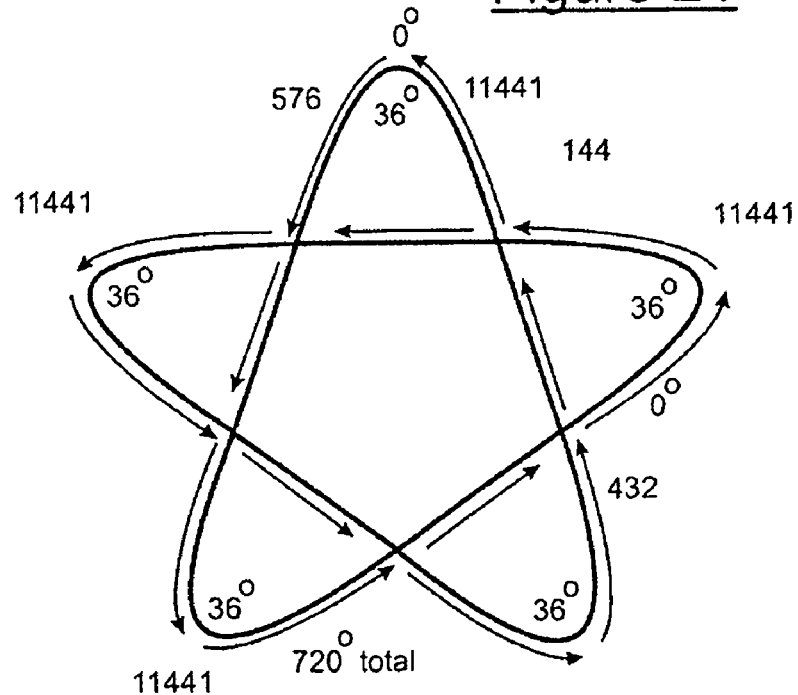

Particular paths according to some embodiments have paths that are most notably characterized by the total of the absolute of the angular displacement over a cycle of the path being more than 360 degrees. As is evident from FIG. 21 a figure of eight has a 540 degree total and a five pointed star has a 720 degree total. These paths are perturbed in the sense that they transverse over more than 360 degrees as compared with 360 degrees as would be the case with elliptical motion. The invention also comprehends triangular paths which would have a 360 degree total.

With triangular paths there are at least two distinct changes in direction over a cycle of oscillation of the pressure stimulus.

Figure 19:
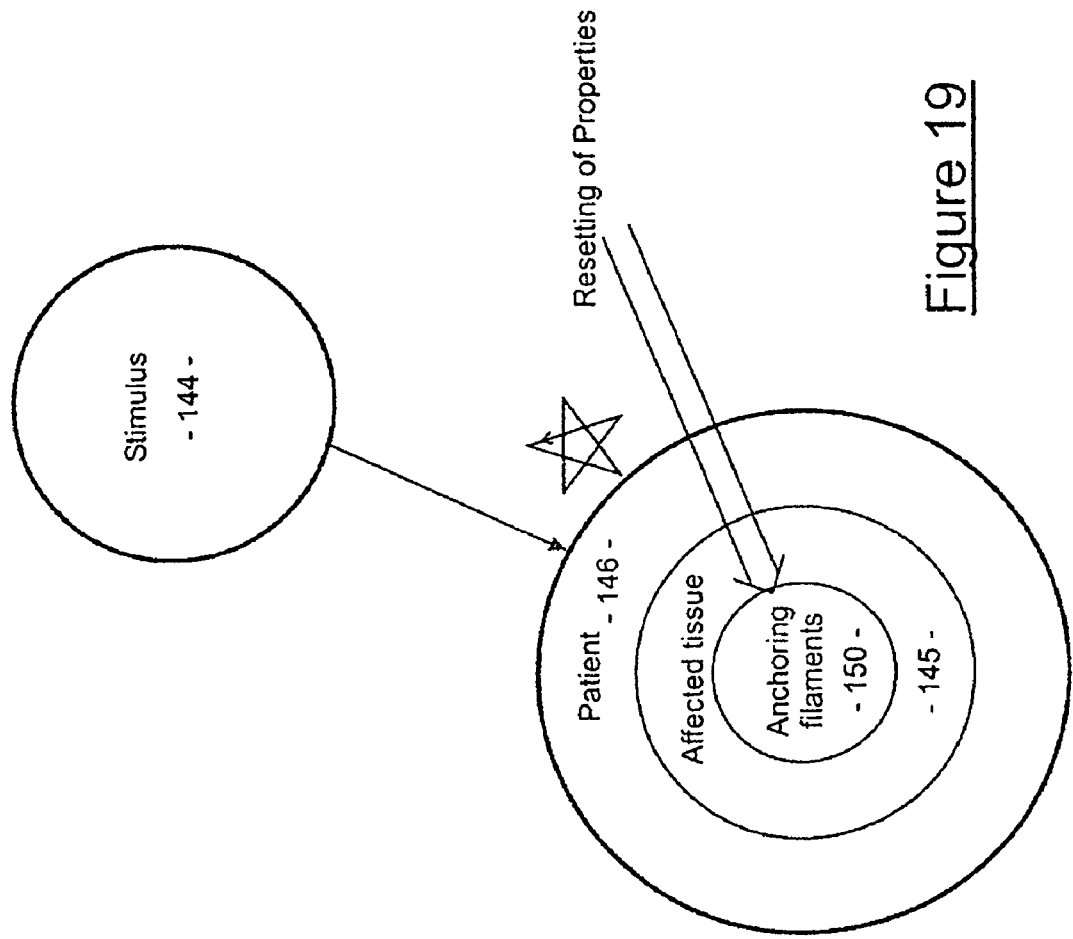
FIG. 19 is a schematic view of a method according to a fifth embodiment.

In related embodiments it has been realised that the anchoring filaments may develop a relaxed memory effectively releasing their hold on the open gates of the initial lymphatics when in a stagnant state. In this embodiment and for the purpose of advantageously working towards the workings of a healthy lymphatic system, the anchoring filaments are strained or flexed in a reciprocating or pulsating manner so that they retain their elastic integrity and functionality. FIG. 19 illustrates the further embodiment wherein a stimulus 144 having variations as described above is applied to a patient 146 having affected tissue 145 whereby anchoring filaments 150 of that affected tissue are exercised.

Thus in this embodiment the patient is subjected to similar pressure variations that are configured to vibrate the anchoring filaments of the initial lymphatics at a rate that is conducive to stimulating a resetting of their elastic properties. By configuring the pressure variations to a particular magnitude and frequency the anchoring filaments can be exercised in a concerted manner. In contradistinction to prior art methods there is a reconditioning of anchoring filaments that have been subjected to a continual strain for extended periods of time due to the increased fluid pressure acting on the body of the initial lymphatics.

It is known that the rate of lymphatic drainage depends on a number of factors including both Myogenic factors and Neurogenic factors. Myogenic factors generally are determined by the presence of the material sought to be removed and Neurogenic factors relate primarily to information coming down the nerves. The respiratory rate and muscular movement of the patient are known to also have an effect. Certain disclosed embodiments show that it is possible to externally generate relatively high interstitial fluid movements through the lymphatic system when then lymphatic system is depressed and that the lymphatic system can, in some circumstances, be reset. The present disclosure relates to the lymphatic system and affected tissue and not merely lymphoedema.

Vibrational massage of the form disclosed herein could just as well be ideally suited for conditions involving poor tissue and cellular health associated with the accumulation of materials in the tissue spaces. Such disorder and disease areas may include but are not limited to myxoedema, lipoedema, poor wound healing, venous oedemas, inflammatory conditions, pressure soars and ulcerations of all causes but specifically those related to diabetes. The present disclosure is not to be taken as limited to lymphoedema.

It should be appreciated that the scope of the invention is not limited to the particular embodiment disclosed herein.

The claims defining the invention are as follows:

1. An apparatus for treating a patient having affected tissue the apparatus comprising:
    an armature having planar opposite sides and provided with a plurality of electrical current paths, the armature being reactive to a force created by a flow of electric current in the current paths and lines of magnetic flux passing through the current paths, the force acting in a single plane of the armature to effect at least two dimensional translational motion of the armature along a motion path in the plane, the armature provided with a central opening extending between the planar opposite sides and completely through the armature; and
    a cuff structure supported by the armature about, and extending into, the opening, wherein the cuff structure is adapted to surround and closely conform to a portion of the patient having the affected tissue that is inserted through the opening of the armature;
    the cuff structure comprising a plurality of individual compartments connected together by a porting system to a reservoir of a pressurized working fluid, wherein the motion of the armature is transferred to the cuff structure and subsequently transferred to the affected tissue.

2. An apparatus according to claim 1 characterized in that the working fluid is pressurized air.

3. An apparatus according to claim 1 wherein a configuration of the motion path is controlled by controlling phase, frequency and amplitude of electric currents supplied to the armature.

4. An apparatus according to claim 3 wherein the motion path has a total absolute angular displacement of more than 360 degrees per cycle of motion of the armature.

5. An apparatus according to claim 4 wherein the total absolute angular displacement at the motion path is about 540 degrees.

6. An apparatus according to claim 4 wherein the total absolute angular displacement over the motion path is about 720 degrees.

7. An apparatus according to claim 1 where-in the motion path comprises at least two changes in direction per cycle of motion of the armature.

8. An apparatus according to claim 1 wherein the armature moves with a frequency that coincides with a resonate frequency of the affected tissue.

9. An apparatus according to claim 1 wherein the armature moves with a frequency that is swept through a range of frequencies.

10. An apparatus according to claim 1 wherein the motion path has a peak to peak amplitude of between 0.1 mm and 5 mm, and a frequency between 10 and 100 hertz.

11. An apparatus according to claim 1 wherein the armature moves at a velocity of about 100 mm per second.

12. An apparatus according to claim 1 wherein the motion path has a peak to peak amplitude of between 0.5 mm and 5 mm, and a frequency of between 11 and 50 hertz.

13. An apparatus according to claim 1 wherein the motion path is arranged within a circular area which substantially avoids traveling back and forth over a central region of the circular area.

14. An apparatus according to claim 1 wherein the motion path consists of five path elements arranged end to end, with each end positioned to lay substantially on a circle, such that the five path elements form a continuous five pointed star.

15. An apparatus according to claim 1 wherein the motion path consists of twenty path elements arranged end to end, with each end positioned to lay substantially on a circle, such that a twenty path elements form a continuous twenty pointed star.

16. An apparatus according to claim 1 characterized in that the motion path is in a shape that resembles a six leaf clover.

17. The apparatus according to claim 1 wherein the motion path contains at least three non-linear points per cycle of motion of the armature.

18. A method of treating a patient having affected tissue comprising:
- coupling a cuff structure comprising a plurality of compartments to an armature, the armature having planar opposite sides and a central opening extending between the planar opposite sides and completely through the armature, wherein the cuff structure is supported about and extends into the opening;
- providing the armature with a plurality of electrical current paths;
- disposing the armature in a magnetic field having lines of magnetic flux that pass through the electrical current paths;
- inserting a portion of the patient having the affected tissue through the opening in the armature wherein the affected tissue is surrounded by the cuff structure;
- inflating the compartments of the cuff structure to closely conform to the portion of the patient; and
- passing an electric current through to the electrical current paths to produce a force acting on the armature to cause motion of the armature in at least two dimensions in a single plane of the armature wherein the motion of the armature is transferred to the cuff structure.

* * * * *